US012605290B2

(12) United States Patent
Greening, II et al.

(10) Patent No.: US 12,605,290 B2
(45) Date of Patent: Apr. 21, 2026

(54) ARTICLE HAVING A BOND PATTERN

(71) Applicant: The Procter & Gamble Company, Cincinnati, OH (US)

(72) Inventors: Nelson Edward Greening, II, Cincinnati, OH (US); Urmish Popatlal Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 415 days.

(21) Appl. No.: 17/341,697

(22) Filed: Jun. 8, 2021

(65) Prior Publication Data

US 2021/0378885 A1      Dec. 9, 2021

Related U.S. Application Data

(60) Provisional application No. 63/036,500, filed on Jun. 9, 2020.

(51) Int. Cl.
| | |
|---|---|
| *A61F 13/539* | (2006.01) |
| *A61F 13/49* | (2006.01) |
| *A61F 13/84* | (2006.01) |

(52) U.S. Cl.
CPC ............ *A61F 13/539* (2013.01); *A61F 13/49* (2013.01); *A61F 13/84* (2013.01); *A61F 2013/53991* (2013.01)

(58) Field of Classification Search
CPC ........ A61F 13/539; A61F 13/49; A61F 13/84; A61F 2013/53991; A61F 13/49012;

(Continued)

(56) References Cited

U.S. PATENT DOCUMENTS

| | | |
|---|---|---|
| 3,113,225 A | 12/1963 | Claus |
| 3,338,992 A | 8/1967 | Allison |

(Continued)

FOREIGN PATENT DOCUMENTS

| | | |
|---|---|---|
| CN | 103209828 A | 7/2013 |
| CN | 104582945 A | 4/2015 |

(Continued)

OTHER PUBLICATIONS

"Oxford English Dictionary, dimension, 2024, Oxford English Dictionary, https://www.oed.com/dictionary/dimension_n?tab=meaning_and_use#6810473" (Year: 2024).*

(Continued)

*Primary Examiner* — Rebecca E Eisenberg
*Assistant Examiner* — Katherine-Ph Minh Pham
(74) *Attorney, Agent, or Firm* — Daniel S. Albrecht; Wednesday G. Shipp

(57) ABSTRACT

An absorbent article includes a first waist region, a second waist region and a crotch region disposed between the first and second waist regions; and a topsheet, a backsheet and an absorbent core disposed between the topsheet and the backsheet. The article further includes a stretch laminate having a bonding region. The bonding region has a plurality of ultrasonic bonds, a majority of the ultrasonic bonds are oriented in a stretch direction, and the bonding region has a Hysteresis Ratio of 2.5 or less and an Unload Force at 50% of 0.44 MPa or greater.

20 Claims, 13 Drawing Sheets

(58) Field of Classification Search
 CPC .............. A61F 13/5633; A61F 13/5638; A61F
  13/4902; B32B 5/022; B32B 27/12
 See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,515,595 A | 5/1985 | Kievit |
| 4,573,986 A | 3/1986 | Minetola et al. |
| 4,610,678 A | 9/1986 | Weisman |
| 4,629,643 A | 12/1986 | Curro |
| 4,634,440 A | 1/1987 | Widlund |
| 4,662,875 A | 5/1987 | Hirotsu |
| 4,673,402 A | 6/1987 | Weisman |
| 4,699,622 A | 10/1987 | Toussant |
| 4,710,189 A | 12/1987 | Lash |
| 4,780,352 A | 10/1988 | Palumbo |
| 4,785,996 A | 11/1988 | Ziecker et al. |
| 4,834,735 A | 5/1989 | Alemany |
| 4,834,741 A | 5/1989 | Sabee |
| 4,842,666 A | 6/1989 | Werenicz |
| 4,846,815 A | 7/1989 | Scripps |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball et al. |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen |
| 5,092,861 A | 3/1992 | Nomura |
| 5,137,537 A | 8/1992 | Herron |
| 5,143,679 A | 9/1992 | Weber |
| 5,147,345 A | 9/1992 | Lavon |
| 5,149,720 A | 9/1992 | Desmarais |
| 5,151,092 A | 9/1992 | Buell |
| 5,156,793 A | 10/1992 | Buell |
| 5,167,897 A | 12/1992 | Weber |
| 5,221,274 A | 6/1993 | Buell |
| 5,242,436 A | 9/1993 | Weil |
| 5,246,433 A | 9/1993 | Hasse |
| 5,260,345 A | 11/1993 | Desmarais |
| 5,266,392 A | 11/1993 | Land |
| 5,269,775 A | 12/1993 | Freeland |
| 5,340,648 A | 8/1994 | Rollins et al. |
| 5,342,338 A | 8/1994 | Roe |
| 5,344,691 A | 9/1994 | Hanschen |
| 5,360,420 A | 11/1994 | Cook et al. |
| 5,376,430 A | 12/1994 | Swenson et al. |
| 5,382,400 A | 1/1995 | Pike et al. |
| 5,387,207 A | 2/1995 | Dyer |
| 5,397,316 A | 3/1995 | Young |
| 5,418,045 A | 5/1995 | Pike et al. |
| 5,422,172 A | 6/1995 | Wu |
| 5,433,715 A | 7/1995 | Tanzer |
| 5,501,756 A | 3/1996 | Rollins et al. |
| 5,507,909 A | 4/1996 | Rollins et al. |
| 5,518,801 A | 5/1996 | Chappell et al. |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,591,155 A | 1/1997 | Nishikawa |
| 5,599,335 A | 2/1997 | Goldman et al. |
| 5,607,414 A | 3/1997 | Richards |
| 5,607,760 A | 3/1997 | Roe |
| 5,609,587 A | 3/1997 | Roe |
| 5,622,772 A | 4/1997 | Stokes |
| 5,628,097 A | 5/1997 | Benson |
| 5,635,191 A | 6/1997 | Roe |
| 5,643,588 A | 7/1997 | Roe |
| 5,658,639 A | 8/1997 | Curro |
| 5,665,300 A | 9/1997 | Brignola |
| 5,674,216 A | 10/1997 | Buell et al. |
| 5,691,034 A | 11/1997 | Krueger |
| 5,700,254 A | 12/1997 | McDowall et al. |
| 5,702,551 A | 12/1997 | Huber et al. |
| 5,707,468 A | 1/1998 | Arnold et al. |
| 5,804,021 A * | 9/1998 | Abuto .................... B32B 27/40 |
| | | 428/152 |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline |
| 5,916,661 A | 6/1999 | Benson |
| 5,957,908 A | 9/1999 | Kline |
| 5,968,025 A | 10/1999 | Roe |
| 5,968,888 A | 10/1999 | Blandiaux |
| 5,972,806 A | 10/1999 | Weinberger |
| 5,993,432 A | 11/1999 | Lodge |
| 6,004,306 A | 12/1999 | Robles |
| 6,030,373 A | 2/2000 | Vangompel |
| 6,036,796 A | 3/2000 | Halbert |
| 6,077,375 A | 6/2000 | Kwok |
| 6,096,668 A | 8/2000 | Abuto |
| 6,107,537 A | 8/2000 | Elder |
| 6,118,041 A | 9/2000 | Roe et al. |
| 6,120,487 A | 9/2000 | Ashton |
| 6,120,489 A | 9/2000 | Johnson |
| 6,123,792 A | 9/2000 | Samida |
| 6,140,551 A | 10/2000 | Niemeyer |
| 6,153,209 A | 11/2000 | Vega et al. |
| 6,169,151 B1 | 1/2001 | Waymouth |
| 6,200,635 B1 | 3/2001 | Kwok |
| 6,235,137 B1 | 5/2001 | Van Eperen et al. |
| 6,255,236 B1 | 7/2001 | Cree |
| 6,310,154 B1 | 10/2001 | Babcock |
| 6,361,634 B1 | 3/2002 | White et al. |
| 6,369,121 B1 | 4/2002 | Catalfamo |
| 6,382,290 B2 | 5/2002 | Mcnichols |
| 6,410,129 B2 | 6/2002 | Zhang |
| 6,426,444 B2 | 7/2002 | Roe et al. |
| 6,428,526 B1 | 8/2002 | Heindel |
| 6,432,098 B1 | 8/2002 | Kline |
| 6,454,989 B1 | 9/2002 | Neely et al. |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,520,237 B1 | 2/2003 | Bolyard, Jr. et al. |
| 6,534,149 B1 | 3/2003 | Daley |
| 6,540,854 B2 | 4/2003 | Couillard |
| 6,551,294 B1 | 4/2003 | Elsberg et al. |
| 6,555,643 B1 | 4/2003 | Rieger |
| 6,559,262 B1 | 5/2003 | Waymouth |
| 6,561,430 B2 | 5/2003 | Ou |
| 6,572,595 B1 | 6/2003 | Klemp |
| 6,572,598 B1 | 6/2003 | Ashton |
| 6,582,518 B2 | 6/2003 | Riney |
| 6,586,652 B1 | 7/2003 | Roe et al. |
| 6,610,161 B2 | 8/2003 | Erdman |
| 6,610,390 B1 | 8/2003 | Kauschke |
| 6,613,146 B2 | 9/2003 | Bolyard, Jr. |
| 6,617,016 B2 | 9/2003 | Zhang et al. |

(56)                References Cited

U.S. PATENT DOCUMENTS

| | | |
|---|---|---|
| 6,627,564 B1 | 9/2003 | Morman |
| 6,627,787 B1 | 9/2003 | Roe et al. |
| 6,632,386 B2 | 10/2003 | Shelley et al. |
| 6,645,330 B2 | 11/2003 | Pargass |
| 6,645,569 B2 | 11/2003 | Cramer |
| 6,649,001 B2 | 11/2003 | Heden |
| 6,652,693 B2 | 11/2003 | Burriss et al. |
| 6,677,258 B2 | 1/2004 | Carroll |
| 6,692,477 B2 | 2/2004 | Gibbs |
| 6,713,159 B1 | 3/2004 | Blenke |
| 6,719,846 B2 | 4/2004 | Nakamura et al. |
| 6,737,102 B1 | 5/2004 | Saidman et al. |
| 6,758,925 B1 | 7/2004 | Stegelmann |
| 6,767,420 B2 | 7/2004 | Stegelmann |
| 6,818,083 B2 | 11/2004 | Mcamish et al. |
| 6,825,393 B2 | 11/2004 | Roe et al. |
| 6,830,800 B2 | 12/2004 | Curro |
| 6,843,134 B2 | 1/2005 | Anderson |
| 6,849,142 B1 | 2/2005 | Goulait |
| 6,861,571 B1 | 3/2005 | Roe et al. |
| 6,863,933 B2 | 3/2005 | Cramer |
| 6,878,433 B2 | 4/2005 | Curro |
| 6,905,488 B2 | 6/2005 | Olson |
| 6,974,514 B2 | 12/2005 | Hamulski |
| 7,056,404 B2 | 6/2006 | Mcfall |
| 7,062,983 B2 | 6/2006 | Anderson |
| 7,087,287 B2 | 8/2006 | Curro et al. |
| 7,108,759 B2 | 9/2006 | You |
| 7,112,621 B2 | 9/2006 | Rohrbaugh |
| 7,270,861 B2 | 9/2007 | Broering |
| 7,291,239 B2 | 11/2007 | Polanco et al. |
| 7,435,243 B2 | 10/2008 | Miyamoto |
| 7,531,233 B2 | 5/2009 | Kling |
| 7,569,039 B2 | 8/2009 | Matsuda |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum |
| 7,819,853 B2 | 10/2010 | Desai |
| 7,824,594 B2 | 11/2010 | Qureshi |
| 7,870,651 B2 | 1/2011 | Middlesworth |
| 7,896,641 B2 | 3/2011 | Qureshi |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi |
| 8,092,438 B2 | 1/2012 | Betts |
| 8,118,801 B2 | 2/2012 | Macura |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai |
| 8,480,642 B2 | 7/2013 | Betts |
| 8,491,557 B2 | 7/2013 | Kline |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman |
| 8,618,350 B2 | 12/2013 | Mansfield |
| 8,679,391 B2 | 3/2014 | Odonnell |
| 8,690,852 B2 | 4/2014 | Macura |
| 8,697,938 B2 | 4/2014 | Roe |
| 8,709,579 B2 | 4/2014 | Hoenigmann |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Mansfield |
| 8,858,523 B2 | 10/2014 | Sauer |
| 8,939,957 B2 | 1/2015 | Raycheck |
| 8,940,116 B2 | 1/2015 | Gilgenbach |
| 9,102,132 B2 | 8/2015 | Wennerbck |
| 9,169,384 B2 | 10/2015 | Autran |
| 9,211,221 B2 | 12/2015 | Macura |
| 9,301,889 B2 | 4/2016 | Miyamoto |
| 9,333,125 B2 | 5/2016 | Kline et al. |
| 9,358,161 B2 | 6/2016 | Lawson |
| 9,434,143 B2 | 9/2016 | Sablone |
| 9,498,941 B2 | 11/2016 | Sablone |
| 9,533,067 B2 | 1/2017 | Schonbeck et al. |
| 9,687,580 B2 | 6/2017 | Schonbeck |
| 9,724,248 B2 | 8/2017 | Hughes |
| 9,821,542 B2 | 11/2017 | Bruce |
| 10,010,645 B2 | 7/2018 | Schonbeck |
| 10,485,713 B2 | 11/2019 | Schonbeck |
| 10,524,964 B2 | 1/2020 | Sauer |
| 10,561,537 B2 | 2/2020 | Lenser et al. |
| 10,568,775 B2 | 2/2020 | Lenser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,799,396 B2 | 10/2020 | Takeuchi |
| 10,959,887 B2 | 3/2021 | Lenser et al. |
| 10,966,876 B2 | 4/2021 | Lenser et al. |
| 11,071,654 B2 | 7/2021 | Lenser et al. |
| 11,083,633 B2 | 8/2021 | Lenser et al. |
| 11,135,100 B2 | 10/2021 | Schönbeck et al. |
| 11,179,278 B2 | 11/2021 | Schönbeck et al. |
| 11,266,543 B2 | 3/2022 | Lenser et al. |
| 11,331,223 B2 | 5/2022 | Lenser et al. |
| 11,382,798 B2 | 7/2022 | Lenser et al. |
| 11,642,248 B2 | 5/2023 | Dalal |
| 11,642,250 B2 | 5/2023 | Lenser et al. |
| 11,998,428 B2 | 6/2024 | Coenen |
| 2001/0018579 A1 | 8/2001 | Klemp |
| 2001/0024940 A1 | 9/2001 | Cook et al. |
| 2002/0095129 A1 | 7/2002 | Friderich |
| 2002/0187696 A1 | 12/2002 | Veiga et al. |
| 2002/0188268 A1 | 12/2002 | Kline |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 | 6/2003 | Gibbs |
| 2003/0120240 A1 | 6/2003 | Buell |
| 2003/0124310 A1 | 7/2003 | Ellis |
| 2003/0148684 A1 | 8/2003 | Cramer et al. |
| 2003/0181120 A1 | 9/2003 | Wu |
| 2003/0233082 A1 | 12/2003 | Kline |
| 2004/0087235 A1 | 5/2004 | Morman |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0209042 A1 | 10/2004 | Peacock |
| 2004/0224132 A1 | 11/2004 | Roe |
| 2005/0008839 A1 | 1/2005 | Cramer et al. |
| 2005/0065487 A1 | 3/2005 | Graef |
| 2005/0107764 A1 | 5/2005 | Matsuda et al. |
| 2005/0154362 A1 | 7/2005 | Warren |
| 2005/0222546 A1 | 10/2005 | Vargo |
| 2005/0245162 A1 | 11/2005 | Mccormack |
| 2005/0287892 A1 | 12/2005 | Fouse |
| 2006/0047260 A1 | 3/2006 | Ashton |
| 2006/0062963 A1 | 3/2006 | Middlesworth |
| 2006/0089616 A1 | 4/2006 | Belau et al. |
| 2006/0135024 A1 | 6/2006 | Thomas |
| 2006/0148361 A1 | 7/2006 | Mccormack |
| 2006/0149209 A1 | 7/2006 | Malchow |
| 2006/0259003 A1 | 11/2006 | Venkitaraman |
| 2006/0271003 A1 | 11/2006 | Loescher |
| 2006/0287637 A1 | 12/2006 | Lam |
| 2006/0288547 A1 | 12/2006 | Jackson |
| 2007/0048497 A1 | 3/2007 | Zhou |
| 2007/0105472 A1 | 5/2007 | Marche |
| 2007/0123124 A1 | 5/2007 | Middlesworth |
| 2007/0141311 A1 | 6/2007 | Mleziva |

(56) References Cited

U.S. PATENT DOCUMENTS

| | | |
|---|---|---|
| 2007/0142798 A1 | 6/2007 | Goodlander |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0234529 A1 | 10/2007 | Middlesworth |
| 2007/0237924 A1 | 10/2007 | Bruce |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge et al. |
| 2008/0003910 A1 | 1/2008 | Hughes |
| 2008/0003911 A1 | 1/2008 | Sabbagh |
| 2008/0045917 A1 | 2/2008 | Autran |
| 2008/0051748 A1 | 2/2008 | Black |
| 2008/0076315 A1 | 3/2008 | Mccormack |
| 2008/0114325 A1 | 5/2008 | Edwall et al. |
| 2008/0119102 A1 | 5/2008 | Hughes |
| 2008/0147031 A1 | 6/2008 | Long |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Iyad |
| 2009/0275909 A1 | 11/2009 | Sakaguchi |
| 2009/0292266 A1 | 11/2009 | Bäck |
| 2009/0294044 A1 | 12/2009 | Gill |
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2009/0326503 A1 | 12/2009 | Lakso |
| 2010/0040826 A1 | 2/2010 | Mansfield et al. |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0222761 A1 | 9/2010 | Westwood et al. |
| 2010/0262105 A1 | 10/2010 | Turner |
| 2010/0262107 A1 | 10/2010 | Turner et al. |
| 2010/0268183 A1 | 10/2010 | Een |
| 2010/0280481 A1 | 11/2010 | Kline |
| 2010/0280484 A1 | 11/2010 | Kline et al. |
| 2010/0285286 A1 | 11/2010 | Middlesworth |
| 2011/0004176 A1 | 1/2011 | Andersson |
| 2011/0040273 A1 | 2/2011 | Sablone |
| 2011/0046594 A1 | 2/2011 | Sablone |
| 2011/0066126 A1 | 3/2011 | Mansfield |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karlson |
| 2011/0151739 A1 | 6/2011 | Bosler |
| 2011/0152812 A1 | 6/2011 | Hird |
| 2011/0178490 A1 | 7/2011 | Lavon |
| 2011/0196332 A1 | 8/2011 | Cheng |
| 2011/0208142 A1 | 8/2011 | Roe |
| 2011/0318987 A1 | 12/2011 | Ooishi |
| 2012/0022490 A1 | 1/2012 | Marche et al. |
| 2012/0045620 A1 | 2/2012 | Oba |
| 2012/0055613 A1 | 3/2012 | Baeck |
| 2012/0055615 A1 | 3/2012 | Baeck |
| 2012/0061015 A1 | 3/2012 | Lavon et al. |
| 2012/0061016 A1 | 3/2012 | Lavon et al. |
| 2012/0095429 A1 | 4/2012 | Kobayashi |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1 | 9/2012 | Lam |
| 2012/0251771 A1 | 10/2012 | Wilson |
| 2012/0252716 A1 | 10/2012 | Barnabas et al. |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | Lavon |
| 2013/0082418 A1 | 4/2013 | Curro |
| 2013/0090623 A1 | 4/2013 | Ohashi |
| 2013/0095279 A1 | 4/2013 | Hauschildt |
| 2013/0144245 A1 | 6/2013 | Roe |
| 2013/0149925 A1 | 6/2013 | Handziak et al. |
| 2013/0158497 A1 | 6/2013 | Yamaguchi |
| 2013/0164480 A1 | 6/2013 | Sakurai |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider et al. |
| 2013/0218116 A1 | 8/2013 | Schneider |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Lenser |
| 2013/0306226 A1 | 11/2013 | Zink |
| 2014/0005628 A1 | 1/2014 | Lavon et al. |
| 2014/0018222 A1 | 1/2014 | Sablone |
| 2014/0018759 A1 | 1/2014 | Jayasinghe |
| 2014/0039434 A1 | 2/2014 | Xu |
| 2014/0041786 A1 | 2/2014 | Henke |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno |
| 2014/0276525 A1 | 9/2014 | Lavon et al. |
| 2014/0330232 A1 | 11/2014 | Schönbeck |
| 2014/0367032 A1 | 12/2014 | Homoelle et al. |
| 2014/0377506 A1 | 12/2014 | Eckstein et al. |
| 2014/0377513 A1 | 12/2014 | Galie |
| 2014/0378924 A1 | 12/2014 | Turner |
| 2015/0032078 A1 | 1/2015 | Collins |
| 2015/0038929 A1 | 2/2015 | Van Malderen |
| 2015/0057630 A1 | 2/2015 | Tange |
| 2015/0126955 A1 | 5/2015 | Sauer |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle |
| 2015/0320611 A1 | 11/2015 | Seitz |
| 2016/0008184 A1 | 1/2016 | Raycheck et al. |
| 2016/0013614 A1 | 1/2016 | Moto |
| 2016/0100999 A1 | 4/2016 | Hamilton |
| 2016/0136014 A1 | 5/2016 | Arora |
| 2016/0167334 A1 | 6/2016 | Arora |
| 2016/0206485 A1 | 7/2016 | Seitz |
| 2016/0228308 A1* | 8/2016 | Schmitz .............. A61F 13/5622 |
| 2016/0270972 A1 | 9/2016 | Surushe |
| 2016/0324697 A1 | 11/2016 | Schoenbeck |
| 2017/0000657 A1 | 1/2017 | Chatterjee |
| 2017/0014279 A1 | 1/2017 | Berrizbeitia |
| 2017/0022339 A1 | 1/2017 | Hanschen et al. |

(56)　　　　　References Cited

U.S. PATENT DOCUMENTS

| | | |
|---|---|---|
| 2017/0027775 A1 | 2/2017 | Barnes |
| 2017/0056256 A1 | 3/2017 | Smith |
| 2017/0071800 A1 | 3/2017 | Schonbeck |
| 2017/0079851 A1 | 3/2017 | Greening, II |
| 2017/0079854 A1 | 3/2017 | Butler |
| 2017/0087029 A1 | 3/2017 | Nelson |
| 2017/0142806 A1 | 5/2017 | Park |
| 2017/0252229 A1 | 9/2017 | Bonelli |
| 2017/0296399 A1 | 10/2017 | Kline et al. |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal |
| 2018/0042778 A1 | 2/2018 | Lenser |
| 2018/0042780 A1 | 2/2018 | Lenser |
| 2018/0042784 A1 | 2/2018 | Koshijima |
| 2018/0042785 A1 | 2/2018 | Dalal |
| 2018/0042786 A1* | 2/2018 | Mueller ............ A61F 13/49015 |
| 2018/0042787 A1 | 2/2018 | Lenser |
| 2018/0271716 A1 | 9/2018 | Dalal |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2019/0125597 A1 | 5/2019 | Sauer et al. |
| 2020/0046576 A1 | 2/2020 | Schonbeck |
| 2020/0179179 A1 | 6/2020 | Lenser |
| 2020/0214363 A1 | 7/2020 | Sakai |
| 2020/0214904 A1* | 7/2020 | Tsunoda .................... B32B 7/03 |
| 2020/0268563 A1 | 8/2020 | Lenser |
| 2020/0397625 A1 | 12/2020 | Sakai |
| 2021/0000656 A1 | 1/2021 | Greening, II |
| 2021/0077315 A1 | 3/2021 | Schönbeck et al. |
| 2021/0077316 A1 | 3/2021 | Schönbeck et al. |
| 2021/0077317 A1 | 3/2021 | Schönbeck et al. |
| 2021/0085532 A1 | 3/2021 | Lenser et al. |
| 2021/0307970 A1 | 10/2021 | Lenser et al. |
| 2021/0330514 A1 | 10/2021 | Lenser et al. |
| 2021/0393453 A1 | 12/2021 | Schönbeck et al. |
| 2022/0233362 A1 | 7/2022 | Lenser et al. |
| 2022/0287887 A1 | 9/2022 | Lenser et al. |
| 2022/0354709 A1 | 11/2022 | Dalal et al. |
| 2024/0197540 A1 | 6/2024 | Greening |
| 2025/0082517 A1 | 3/2025 | Dalal et al. |

FOREIGN PATENT DOCUMENTS

| | | |
|---|---|---|
| CN | 104703567 A | 6/2015 |
| CN | 104797228 A | 7/2015 |
| CN | 103434239 B | 11/2015 |
| CN | 204909840 U | 12/2015 |
| CN | 104837455 B | 4/2018 |
| CN | 108601686 A | 9/2018 |
| EP | 0666308 A2 | 8/1995 |
| EP | 1256594 A1 | 11/2002 |
| EP | 1447066 A1 | 8/2004 |
| EP | 2100575 A2 | 9/2009 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3170884 A1 | 5/2017 |
| EP | 3246443 A1 | 11/2017 |
| EP | 2647360 B1 | 6/2018 |
| EP | 3639801 | 4/2020 |
| EP | 3251642 B1 | 8/2020 |
| JP | 2004223238 A | 8/2004 |
| JP | 2006112024 A | 4/2006 |
| JP | 2007521036 A | 8/2007 |
| JP | 2011139843 A | 7/2011 |
| JP | 4934835 B2 | 3/2012 |
| JP | 5036641 B2 | 7/2012 |
| JP | 2012524645 A | 10/2012 |
| JP | 2017065142 A | 4/2017 |

| | | |
|---|---|---|
| JP | 6240733 B1 | 11/2017 |
| WO | 9115365 A1 | 10/1991 |
| WO | 9510996 A1 | 4/1995 |
| WO | 95010996 A1 | 4/1995 |
| WO | 9511652 A1 | 5/1995 |
| WO | 9516746 A1 | 6/1995 |
| WO | 9828123 A1 | 7/1998 |
| WO | 9919449 A1 | 4/1999 |
| WO | 2000045763 A1 | 8/2000 |
| WO | 2000059430 A1 | 10/2000 |
| WO | 0073031 A1 | 12/2000 |
| WO | 2002067809 A2 | 9/2002 |
| WO | 2003007864 A1 | 1/2003 |
| WO | 2004017882 A2 | 3/2004 |
| WO | 2004017885 A1 | 3/2004 |
| WO | 2004041990 A1 | 5/2004 |
| WO | 2004060652 A1 | 7/2004 |
| WO | 2006020690 A1 | 2/2006 |
| WO | 2006124337 A1 | 11/2006 |
| WO | 2006138725 A2 | 12/2006 |
| WO | 2007036907 A3 | 4/2007 |
| WO | 2008023291 A3 | 2/2008 |
| WO | 2008026106 A2 | 3/2008 |
| WO | 2008156075 A1 | 12/2008 |
| WO | 2009082277 A1 | 7/2009 |
| WO | 2009146307 A1 | 12/2009 |
| WO | 2010055699 A1 | 5/2010 |
| WO | 2010118214 A1 | 10/2010 |
| WO | 2010126415 A1 | 11/2010 |
| WO | 2011080643 A2 | 7/2011 |
| WO | 2011125893 A1 | 10/2011 |
| WO | 2012030571 A2 | 3/2012 |
| WO | 2012052172 A1 | 4/2012 |
| WO | 2012112501 A1 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | 2013163141 A1 | 10/2013 |
| WO | 2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | 2016073713 A1 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

PCT Search Report and Written Opinion for PCT/US2021/036328 dated Oct. 1, 2021, 13 pages.

All Office Actions; U.S. Appl. No. 15/674,561, filed Aug. 11, 2017.

All Office Actions; U.S. Appl. No. 15/674,596, filed Aug. 11, 2017.

All Office Actions; U.S. Appl. No. 16/748,885, filed Jan. 22, 2020.

All Office Actions; U.S. Appl. No. 16/916,655, filed Jun. 30, 2020.

All Office Actions; U.S. Appl. No. 17/195,677, filed Mar. 9, 2021.

All Office Actions; U.S. Appl. No. 17/195,679, filed Mar. 9, 2021.

All Office Actions; U.S. Appl. No. 17/720,363, filed Apr. 14, 2022.

All Office Actions; U.S. Appl. No. 17/869,815, filed Jul. 21, 2022.

All Office Actions; U.S. Appl. No. 18/485,494, filed Oct. 12, 2023.

Unpublished U.S. Appl. No. 18/485,494, filed Oct. 12, 2023, to Todd Douglas Lenser, et al.

All Office Actions; U.S. Appl. No. 18/588,370, filed Feb. 27, 2024; See Patent Center.

All Office Actions; U.S. Appl. No. 18/960,162, filed Nov. 26, 2024; See Patent Center.

(56)          References Cited

OTHER PUBLICATIONS

Oxford English Dictionary, dimension, Online retrieved from "https://
www.oed.com/dictionary/dimension_n?tab=meaning_and_use#68
10473", 2024, 02 pages.

* cited by examiner

ARTICLE HAVING A BOND PATTERN

CROSS-REFERENCE TO RELATED APPLICATIONS

This application claims the benefit, under 35 USC 119(e), to U.S. Provisional Patent Application No. 63/036,500, filed on Jun. 9, 2020 (P&G 15693P), which is herein incorporated by reference in its entirety.

FIELD OF THE INVENTION

The present disclosure relates to bonded laminates, specifically stretchable laminates such as stretchable laminates found in absorbent articles.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use extensible areas, such as stretch side panels (i.e., ears), within the article to help achieve a snug fit. When worn, the stretch ears extend the article about the hip and waist of the wearer to anchor the product in use while still allowing the wearer to move comfortably. A fastening system is typically joined to the ear to further secure the product about the wearer. Stretch ears are typically laminates of coverstock materials (such as nonwovens) and elastomeric materials.

It has been proposed to create stretch laminates using ultrasonic bonding. In such instance, a stretched elastomeric material is combined with a nonwoven via ultrasonic bonding. After combination, the nonwoven will form corrugations when the laminate is in a relaxed state. In other instances, an elastomeric material is joined in a relaxed state to an extensible or elastic nonwoven via ultrasonic bonding. These laminates can produce highly stretchable ears (depending on the level of stretch imparted in the elastomeric material and/or the extensibility of the nonwoven) while avoiding the use of glues and mechanical activation. However, ultrasonically bonded ears may lack the strength of ears formed under different means (e.g., adhesive bonding, coextrusion). During application, if the ears lack necessary strength, components of the ear and/or the entire ear laminate may tear or delaminate, a fastener may become detached from the ear, and/or the ear may detach from the rest of the article. Such failures render the article itself unusable.

Thus, suitable high bond strength is necessary. Likewise, it is important to balance such strength with required extensibility. In other words, the number and the positioning of bonds must not inhibit stretchability. Moreover, a laminate must stretch sufficiently to permit easy application of the article, while maintaining suitable integrity to stay in position during use. Further, manufacturers also seek to vary patterns for comfort, breathability, aesthetic appeal and product line differentiation.

Therefore, there is a continued need for stretch laminates having improved patterns that provide suitable strength, stretchability and recovery. Moreover, there is a need for variability in the design of such patterns. There is also a need for bond patterns that can be used to create desired properties in a cost effective and efficient manner.

SUMMARY OF THE INVENTION

The invention comprises the features of the independent claims herein. An absorbent article comprises a stretch laminate comprising a nonwoven and an elastomeric layer. The stretch laminate comprises a bonding region. The bonding region comprises a first plurality of ultrasonic bonds, wherein a majority of the bonds in the first plurality are oriented in a stretch direction and each ultrasonic bond in the first plurality comprises at least one dimension that is 0.7 mm or greater. The bonding region comprises a Hysteresis Ratio of 2.5 or less and an Unload Force at 50% of 0.44 MPa or greater as measured by the Hysteresis Test Method herein.

An absorbent article comprises a front waist region, a rear waist region and a crotch region disposed between the first and second waist regions; and a topsheet, a backsheet and an absorbent core disposed between the topsheet and the backsheet. The article further comprises a stretch laminate. The stretch laminate comprises a first bonding region having a plurality of ultrasonic bonds, wherein the majority of bonds in the first plurality are stretch direction oriented; and a second bonding region having a second plurality of bonds, wherein the majority of bonds in the second plurality are oriented in a second direction, perpendicular to the stretch direction. The second bonding region comprises a Low Stress Region.

An absorbent article comprises a first waist region, a second waist region and a crotch region disposed between the first and second waist regions; and a chassis comprising a topsheet, a backsheet and an absorbent core disposed between the topsheet and the backsheet. The article further comprises a stretch laminate. The stretch laminate comprises a nonwoven layer and an elastomeric layer. The stretch laminate may have a bonding region having a plurality of stretch direction oriented ultrasonic bonds with a 10-Hour Force Drop of less than 65%, and a Growth in Aperture of 50% or less after 10 hours.

DETAILED DESCRIPTION OF THE INVENTION

Definitions

Figure 1A:
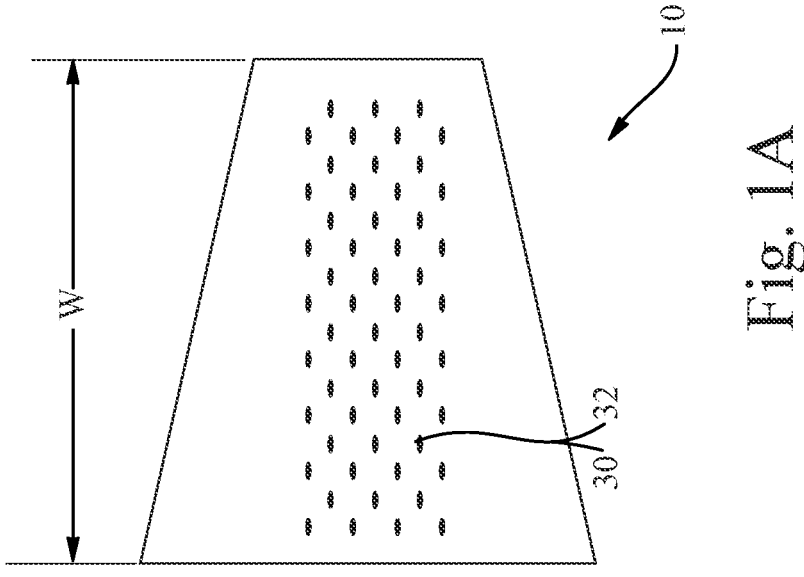
FIG. 1A is a plan view of an exemplary ear according to one nonlimiting embodiment of the present invention.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Aspect ratio" as used herein means the product of the major dimension (i.e., the greatest dimension) of a bond divided by the dimension of the bond that is normal to said major dimension as specified by the Bond Dimensions Test Method herein.

"Elastic," "elastomeric," and "elastically extensible" mean the ability of material, or portion of the material, stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic. As used herein, a laminate is elastic if at least 20% of the area of the laminate meets the elastic definition herein. In this situation, the percent of area of the laminate is determined when the laminate is in a fully stretched state.

"Extensible" means the ability to stretch or elongate, without rupture or breakage, by at least 50% as per step 5(a) in the Hysteresis Test herein. As used herein, a laminate is extensible if at least 20% of the area of the laminate meets the extensible definition herein. In this situation, the percent of area of the laminate is determined when the laminate is in a fully stretched state. If a laminate does not meet the definition of elastic above, but does meet the definition of extensible provided in this paragraph, the laminate is an extensible laminate.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" means a sheet-like material wherein the length and width of the material far exceed the thickness of the material (e.g., 10×, 50×, or even 1000× or more). Films are typically liquid impermeable but may be configured to be breathable.

"Fully stretched" in reference to a laminate means (1) for corrugated laminates, the laminate is fully stretched when corrugations are substantially flattened by extending the laminate while making sure that the inelastic substrates of the laminate are not plastically deformed, and (2) for laminates without corrugations, the laminate is considered fully stretched without any such extension (i.e., noncorrugated laminates are fully stretched in their relaxed state).

"Laminate" means two or more materials that are bonded to one another by any suitable method known in the art (e.g., adhesive bonding, thermal bonding, or high pressure bonding using non-heated or heated patterned roll).

"Longitudinal" as used herein means the maximum linear dimension of the absorbent article in the x-y plane of the article. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article. The longitudinal direction of any component of the absorbent article (e.g., an ear, a waistband) is determined when the component is joined to the article.

"Lateral" refers to a direction generally perpendicular to the longitudinal direction. In the absorbent article described herein, the lateral direction runs substantially parallel from a side edge to an opposing side edge.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" in reference to a laminate means at rest with substantially no external force acting on the laminate, other than gravity.

"Stretch direction" as used herein means the intended direction of extensibility in the final product. For example, a back ear in an absorbent article may be intended to be extensible in the lateral direction to conform around the waist of the wearer. The stretch direction of a laminate may be lateral and/or longitudinal. It is to be appreciated that a product may be stretchable in multiple directions. In such cases, the stretch direction is the primary intended direction of stretch in response to the expected application of force required for use.

"Second direction" as used herein means the direction perpendicular to the stretch direction.

"Oriented" as used herein in reference to a bond being oriented in a particular direction means the bond has an aspect ratio of at least 1.1 with the major dimension forming an angle of 40 degrees or less with a line parallel to said particular direction. By way of example, a stretch direction oriented bond means the bond has a major dimension that forms angle of 40 degrees or less with a line extending in the stretch direction. A second direction oriented, or perpendicularly-oriented, bond means the bond has an aspect ratio of at least 1.1 with the major dimension forming an angle of 40 degrees or less with a line extending in the second direction.

Laminate

Figure 1:
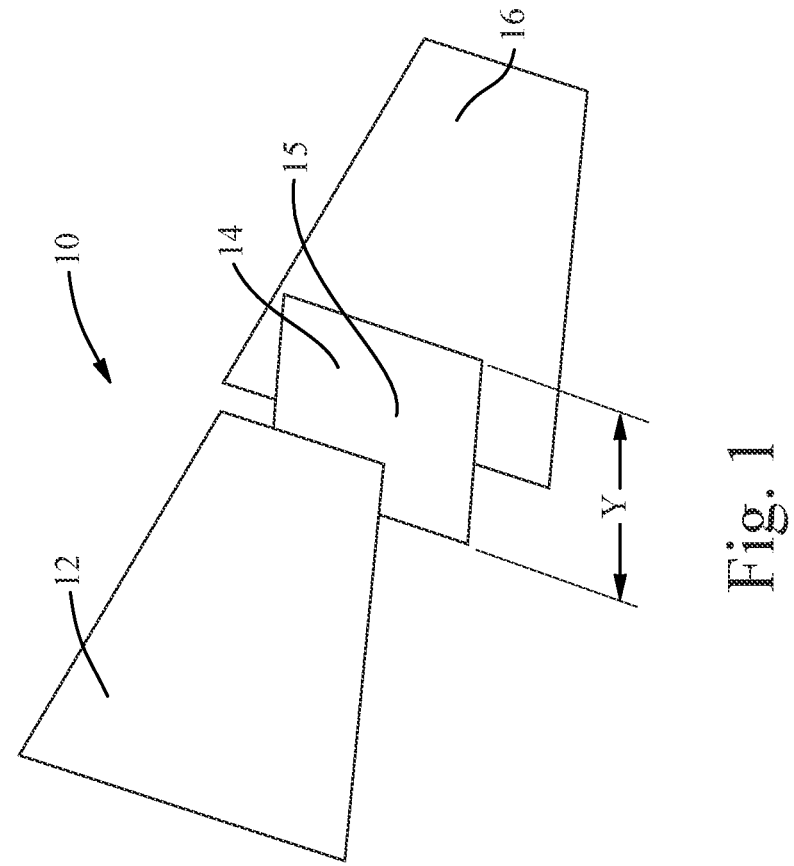
FIG. 1 is an exploded perspective view of an exemplary ear according to a nonlimiting embodiment of the present invention.

As shown in FIG. 1, a laminate 10 comprises a first nonwoven 12 and an elastomeric layer 14. The laminate may comprise a second nonwoven 16, and the elastomeric layer 14 may be sandwiched between the first and second nonwoven. Additional layers may be included (e.g., additional nonwovens, inelastic materials, elastic or extensible materials, etc.). The laminate may be extensible. In certain embodiments, the laminate is elastomeric. One or more laminate layers may be joined by a plurality of ultrasonic bonds 30 as illustrated in FIG. 1A. The ultrasonic bonds may join nonwoven layers through the elastomeric layer. The ultrasonically bonded laminate may be formed by any suitable processes, including but not limited to those described in commonly assigned U.S. Patent App. Nos. 62/374,010, 62/419,515.

Any suitable nonwoven may be used in the laminate 10. Suitable nonwovens may comprise a basis weight of at least about 8 gsm, or about 30 gsm or less, or about 22 gsm or less, or about 17 gsm or less, or from about 10 gsm to about 22 gsm, reciting for said range every 1 increment therein. Suitable nonwoven include but are not limited to spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers, as known in the art. In nonlimiting examples, a nonwoven comprises a meltblown layer. Additionally, or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens in the ear may be void of meltblown layers. While meltblown layers have been found to enhance bonding in ears requiring adhesive (given the meltblown layer's inhibition of the adhesive's diffusion through the porous nonwoven structure), meltblown layers often lack strength. In some embodiments, a nonwoven consists essentially of spunbond layers. In some nonlimiting examples, both the first and the second nonwoven comprises at least 2 spunbond layers, or 3 or more spunbond layers.

The nonwoven web may be formed predominately of polymeric fibers. In some examples, suitable nonwoven fiber materials may include, but are not limited to polymeric materials such as polyolefins, polyesters, polyamide, or specifically, polypropylene (PP), polyethylene (PE), polylactic acid (PLA), polyethylene terephthalate (PET) and/or blends thereof. In some examples, the fibers may be formed of PP/PE blends such as described in U.S. Pat. No. 5,266, 392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and Ser. No. 13/005,237. The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers. Further, the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bicomponent fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or both nonwoven layers because they can feel particularly soft to the touch (for wearer comfort on the inside and aesthetically pleasing feel on the outside) and are generally quite pliable. In other nonlimiting examples, a nonwoven may be void of crimped fibers.

Where the laminate 10 comprises more than one nonwoven, the nonwovens may comprise the same basis weight or different basis weights. Likewise, the nonwovens may comprise the same layer configuration (e.g., SSS) or different layer configurations (e.g., SMS).

The elastomeric layer 14 comprises one or more elastomeric materials which provide elasticity to at least a portion of the layer 14. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618, 350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc., Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

In nonlimiting examples, the elastomeric layer 14 comprises a film 15. The film may comprise a single layer or multiple layers. The film may be extensible or may be elastic in the lateral direction and/or in the longitudinal direction. The film may be preactivated as disclosed, for example, in U.S. Pat. No. 9,533,067.

The elastomeric layer may be shorter in one or more dimensions of the laminate than the laminate itself. For example, the elastomeric layer may comprise a first dimension, Y, and Y may be less than a dimension, W, of the laminate in the same direction by at least about 10 mm. In certain embodiments, Y is at least about 20% of, or from about 25% to about 100%, or from about 35% to about 85%, or about 80% or less of W, reciting for each range every 5% increment therein. Additionally, or alternatively, the elastomeric layer may have a dimension that is equal to one or more dimensions of the laminate. For example, the elastomeric layer may comprise substantially the same longitudinal length of the laminate throughout the lateral width of the laminate. In some embodiments, the elastomeric layer may have a basis weight of from about 5 to about 150 gsm, or from about 10 to about 100 gsm, or less than about 150 gsm, reciting for each range every 5 gsm increment therein.

Figure 2:
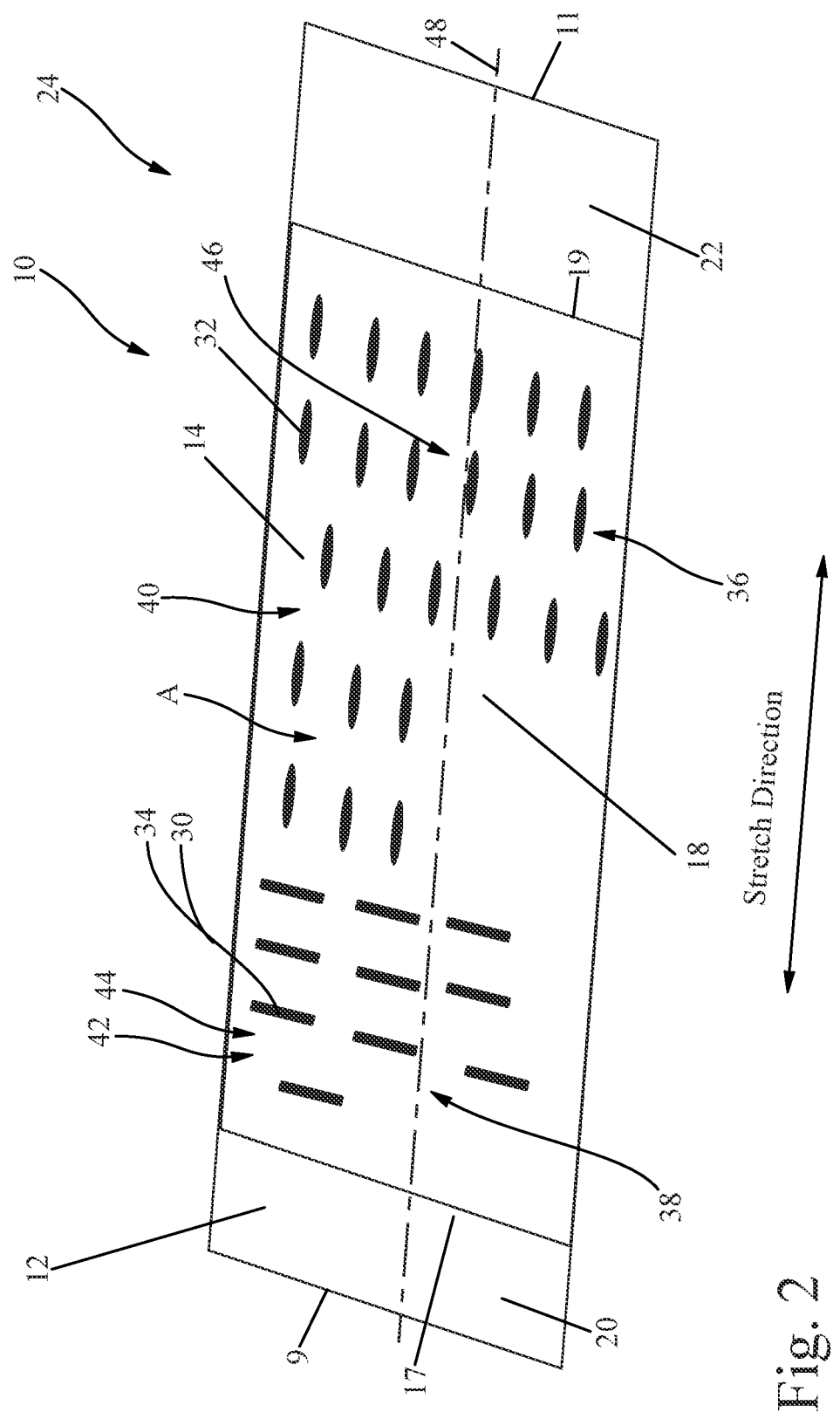
FIG. 2 is a plan view of an exemplary laminate according to a nonlimiting embodiment of the present invention.

Turning to FIG. 2, the laminate 10 may comprise an elasticized region 18. The elasticized region 18 is generally defined by the perimeter of the elastomeric material 14. In the elastic region, the laminate is elastically extensible. In some embodiments, the area of the elastic region comprises at least about 20% of, or from about 30% to about 100%, or about 80% or less of the total area of the laminate, reciting for said range every 5% increment therein.

The laminate may further comprise one or more inelastic regions. In certain embodiments, the laminate 10 comprises a first inelastic region 20, which extends laterally outward from a first laminate edge 9 of the laminate and is adjacent to the elastic region 18 at a first elastomeric material edge 17. The ear may further include a second inelastic region 22, which may extend laterally inward from a second laminate edge 11 and may be adjacent to the elastic region 18 at a second elastomeric material edge 19. The first and second inelastic regions may be made of the same material(s) or different materials.

In certain embodiments, the laminate 10 comprises a gathered laminate 24, wherein one of the layers is strained to a greater degree than a remaining layer during lamination. In this way, the less extensible layer (i.e., the nonwoven 12, 16) will form gathers when the laminate 24 is in a relaxed state. In some embodiments, at least a portion of the elastomeric layer is strained while the nonwoven(s) are in a relaxed state during lamination. The elastomeric layer may be stretched one or more directions. Corrugations then form in the nonwoven layer(s) when the subsequently formed laminate 24 is in a relaxed state. When making gathered laminates, the elastomeric layer is stretched in the stretch direction (i.e., the intended direction of stretch in the final product). The stretch direction may be lateral. In nonlimiting examples, the elastomeric layer is stretched in a direction corresponding with the lateral direction of the article. In other words, when the laminate is joined to the chassis subsequent to lamination, the laminate will be oriented such that the laminate is stretchable in the lateral direction of the article (i.e., the laminate is laterally-extensible).

As shown in FIGS. 1A-3, two or more laminate layers are joined by one or more ultrasonic bonds 30. The ultrasonic bonds may join the nonwoven layers through the elastomeric layer. The bonds may be any suitable shape or size. In some embodiments, bonds are non-circular. Additionally, or alternatively, bond may have longitudinal dimensions that are greater than their lateral dimensions or vice versa. At least a portion of bonds may have an aspect ratio that is at least 1.1, or at least about 1.25, or at least about 1.5, or from about 1.1 to about 10, or from about 1.25 to about 7.5, reciting for each range every 0.01 increment therein. A bond may have a major dimension (i.e., greatest dimension) of at least about 0.55 mm, or at least about 0.7 mm, or at least about 1 mm, or from about 0.55 mm to about 2.6 mm, or from about 1 mm to about 2.5 mm, reciting for said range each 0.05 increment therein. In nonlimiting examples, the major dimension is at least about 0.7 mm A bond may have a minor dimension of at least about 0.5 mm, or at least about 0.75 mm, or from about 0.5 mm to about 2.2 mm, reciting for each range every 0.05 mm increment therein. In nonlimiting examples, bonds have at least one dimension that 0.7 mm or greater, said dimension may be a dimension other than the minor or major dimension. One or more bonds may have a curvilinear shape, such as an elliptical, oval or rod-like shape. Other nonlimiting examples of bond shapes include rectangles, trapezoids, rhombuses, S-shaped and combinations thereof.

Further to the above, one or more ultrasonic bonds 30 are stretch direction oriented bonds 32 (i.e., oriented in the stretch direction). In nonlimiting examples, a majority of the ultrasonic bonds are oriented in the stretch direction. In certain embodiments, at least about 20%, or at least about 30%, or at least about 40% or at least about 50%, or at least about 55%, or from about 20% to about 100%, or about 25% to about 80%, or about 30% to about 75% of the bonds may be stretch direction oriented, reciting for said range every 1% increment therein. Without being bound by theory, it is believed that having a majority of bonds stretch direction oriented provides the laminate with improved return (i.e., unload) forces, reduced tearing and providing greater durability. When such a laminate is stretched, film between bond sites is stretched. Generally, with ultrasonically bonded laminates, each bond site comprises an aperture in the elastomeric material, through which nonwovens or other material layers are bonded. Bonds oriented in the second direction 34 have relatively large bond lengths perpendicular to the stretch direction SD. This longer bond length results in large amounts of elastomeric material becoming disconnected in the stretch direction. Because of this lack of connectivity, when tension is applied in the stretch direction a large aperture forms as the initial bond aperture is incapable of resisting the applied forces. Conversely, stretch direction oriented bonds 32 have relatively small bond lengths perpendicular to the stretched direction SD. This small bond length results in limited amounts of elastomeric material becoming disconnected in the stretch direction. Because of high amount of connectivity, when tension is applied in the stretch direction there sufficient connected material to resist the applied forces resulting in minimal aperture growth. The smaller apertures can lead to improved extensibility and appearance without undermining the integrity of the laminate.

The laminate may be elastic in the stretch direction. The laminate may comprise an area A having a 10-Hour Force Drop of about 65% or less, or about 60% or less, or from about 40% to about 70% reciting every 0.5% increment therein, as measured by the Force Drop Test Method herein. The area A may be at least 25.4 mm in width and 25.4 mm in length. Without being bound by theory, it is believed laminates having a 10-Hour Force Drop as indicated above have improved extensibility and integrity. The desired 10-Hour Force Drop may be obtained through a combination of bond pattern, bond orientation and material chemistries.

In nonlimiting examples, the laminate may not have substantial growth in the elastomeric material aperture, substantial growth being more than about 50% or the original aperture area. In nonlimiting examples, the laminate film has a Growth in Aperture of about 50% or less, or about 25% or less after 10 hours, according to the 10-Hour Force Drop Method.

Additionally, or alternatively, the laminate 10 may comprise a Bond Density of at least about 1.5%, or at least about 2%, or from about 1.5% to about 12% reciting for said range every 1% increment therein as defined by the Bond Dimensions Test Method. The Bond Density may vary depending on the component into which the laminate is incorporated.

Without being bound by theory, it is believed that orientations; geometries including bond aspect ratio, bond area, bond size; and material compositions as disclosed herein result in improved laminate performance. While various shapes may be employed, bonds and substrates according to the teachings herein achieve desired performance. In some embodiments, laminates of the present invention comprise a bonding region 40 having a Hysteresis Ratio of about 3 or less, or about 2.75 or less, about 2.65 or less, or about 2.5 or less, or about 2.4 or less, or from about 1 to about 3. In this way, the laminate demonstrates high resilience. When incorporated into absorbent articles, laminates having Hysteresis Ratios of the present invention have sufficient ability to easily stretch for application and endure forces when worn (e.g., after application, stretch ears relax allowing the product to snuggly conform to the wearer). In other words, the laminate requires relatively lower force to apply but maintains a suitable, higher return force which allows it to endure strain during wear without sagging or tearing.

In addition, the bonding region comprises an Unload Force at 50% of about 0.57 N/in or greater, or about 0.6 N/in or greater, or about 0.62 N/in or greater, or about 0.65 N/in or greater in nonlimiting examples. In some embodiments, it may be desirable to have a higher unload force even if a lower Hysteresis Ratio (3 or less) cannot be achieved. For such embodiments, the laminate comprises an Unload Force at 50% of about 0.4 N/in or greater, or about 0.5 N/in or greater, or about 0.6 N/in or greater, or from about 0.4 N/in to about 2 N/in, reciting for said range every 0.1 N/in increment therein, as measured by the Hysteresis Test Method herein.

The bonding region comprises an Unload Force at 50% of about 0.42 MPa or greater, or about 0.44 MPa or greater, or about 0.45 MPa or greater, or about 0.48 MPa or greater in nonlimiting examples. Additionally, or alternatively, the laminate comprises an Unload Force at 50% of 0.29 MPa or greater, or 0.37 MPa or greater, or 0.44 MPa or greater, or from about 0.29 to about 1.46 MPa, reciting for said range every 0.05 MPa increment therein, as measured by the Hysteresis Test Method herein.

In some embodiments, the laminate may comprise bonds 34 oriented in the second direction (also referred herein to as perpendicularly-oriented bonds 34). In nonlimiting examples, at least 5%, or at least 25%, or at least 50%, or at least about 75%, or from about 5% to about 75% of the bonds may be perpendicularly-oriented, reciting for said range every 5% increment therein. In nonlimiting examples, the average major dimension of stretch direction oriented bonds 32 may be higher than the average major dimension of perpendicularly-oriented bonds 34. For instance, one or more stretch direction oriented bonds may have a major dimension (or in the aggregate, an average major dimension) of about 1.5 mm, and one or more perpendicularly-oriented bonds may have a major dimension (or in the aggregate, an average major dimension) of about 1.2 mm.

Figure 2A:
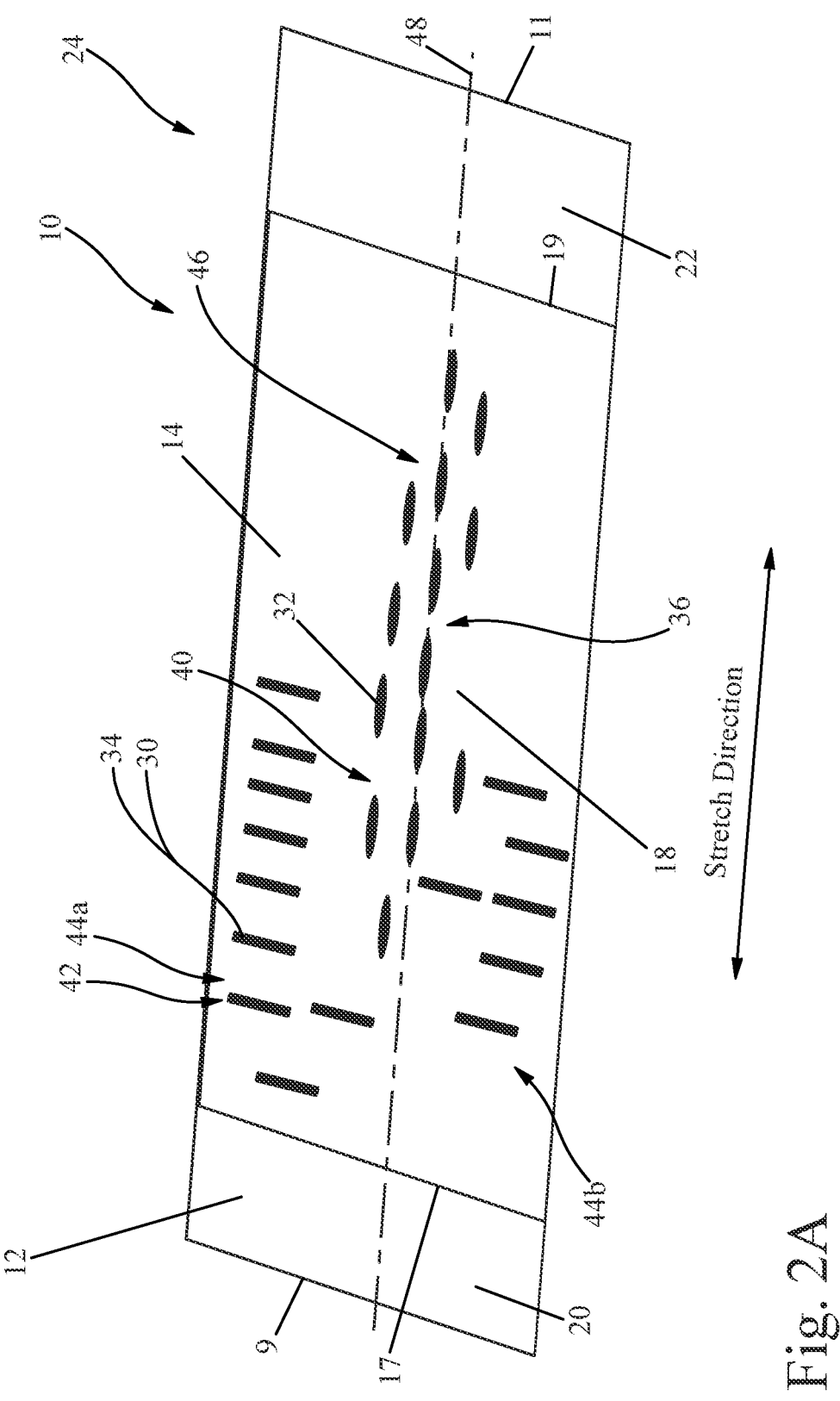
FIG. 2A is a plan view of an exemplary laminate according to another nonlimiting embodiment of the present invention.

Additionally, or alternatively, the laminate may comprise a first plurality of bonds 36, wherein the majority of bonds in the first plurality are stretch direction oriented bonds 32. The laminate may comprise a second plurality of bonds 38 wherein a majority of bonds in the second plurality comprise second direction oriented bonds 34. In this way, the second direction oriented bonds which have lower return forces (resulting in less pressure applied to the wearer) can be used while still maintaining the strength, higher return forces and tear resistance benefits of the stretch direction oriented bonds. The first plurality may be disposed in a first bonding region 40 and/or the second plurality may be disposed in a second bonding region 42, as shown in FIGS. 2-2A. In nonlimiting examples, the second bonding region comprises a low stress region 44. A low stress region has a Load Force at 50% that is at least 10% lower than the Load Force at 50% of an adjacent bonding region (i.e., the adjacent high stress region 46), as measured by the Hysteresis Test Method herein. In nonlimiting examples, the low stress region comprises a Load Force at 50% of about 2 N/in or less, or about 1.5 N/in or less, or about 1.3 N/in or less, or about 1 N/in or less, or about 0.2 N/in to about 2 N/in, reciting for said range every 0.1 N/in increment therein, as measured by the Hysteresis Test Method. The low stress region may comprise a Load Force at 50% of about 1.46 MPa or less, or about 1.10 MPa or less, or about 0.95 MPa or less, or about 0.73 MPa or less, or from about 0.15 MPa to about 1.46 MPa, reciting for said range every 0.05 MPa increment therein, as measured by the Hysteresis Test Method herein. The higher stress region 46 may be disposed centrally in the laminate and may overlap a lateral centerline 48 of the laminate. The low stress region may be at least partially disposed longitudinally outboard and/or longitudinally inboard of the higher stress region. In nonlimiting examples shown in FIG. 2A, the laminate includes two low stress regions 44a and 44b, one disposed longitudinally outboard of the higher stress region and a second disposed longitudinally inboard of the higher stress region. The two low stress regions may comprise the same stress/strain profile or different stress/strain profiles. In nonlimiting examples, the laminate may comprise a gradient in the proportion of second direction bonds. The aggregate area of second direction oriented bonds and/or the number of second direction oriented bonds may increase away further away from the highest stress points of the laminate. For instance, at the highest stress area, the laminate's bonding region may comprise only, or a majority of, stretch direction oriented bonds. Longitudinally inboard, and/or longitudinally outboard of the highest stress area, the laminate's bonding region(s) may gradually increase in the number of second direction oriented bonds, the aggregate area of the second direction oriented bonds, the average size of the dimension in the second direction of the bonds, and/or the average aspect ratio of the bonds where the greater dimension is in the second direction.

Figure 3:
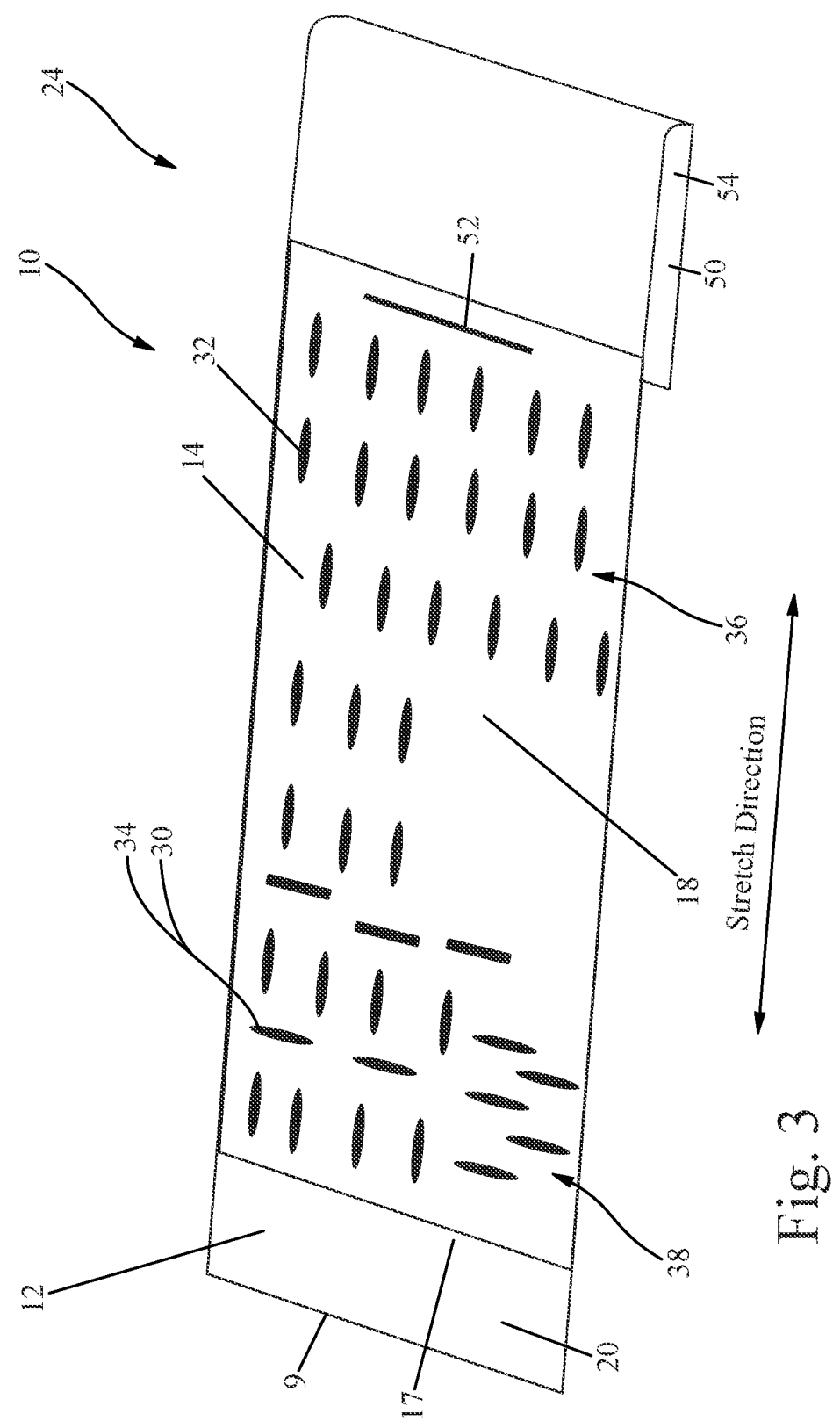
FIG. 3 is perspective view of an exemplary laminate according to another nonlimiting embodiment of the present invention.

In certain embodiments, the first plurality 36 may be at least partially interspersed and/or in at least partial overlapping relationship with the second plurality 38, as illustrated in FIG. 3.

The laminate 10 may further comprise a reinforcing feature 50, which aids in providing strength to the laminate. Nonlimiting examples of reinforcing features include additional bonding 52 such as adhesive, heat or pressure bonding; additional substrate layers 54 including separate material layers and/or folded material; and combinations thereof as shown in FIG. 3. Additional substrate layers 54 may comprise nonwovens, elastomeric materials or combinations thereof. An additional substrate layer 54 may comprise the same material as the first nonwoven, second nonwoven and/or elastomeric layer; or the additional substrate layer 54 may comprise a different material from any of the aforementioned layers.

In certain embodiments, the laminate may comprise an Breathability Value of at least about 1 m³/m²/min, or from about 1 m³/m²/min to about 125 m³/m²/min, or from about 2 m³/m²/min to about 50 m³/m²/min according to the Air Permeability Test Method herein, reciting for each range every 1 m³/m²/min increment therein.

In some embodiments, the laminate may be void of adhesive.

EXAMPLES

The following laminate examples demonstrate properties of the invention herein. The following examples are various combinations of three different laminates, which differ by their elastomeric layers, and 8 different patterns, shown in FIGS. 4A-4H.

Comparative Example 1A comprises a first nonwoven and second nonwoven, and an elastomeric film sandwiched between the first and second nonwoven. Each of the first and second nonwoven are 19 gsm spunbond nonwoven available from Avgol, USA under tradename AVMN3002394. The nonwovens have an average basis weight of about 19 gsm as measured by the Basis Weight Test Method herein. The elastomeric film is available from Berry Global under the tradename under the trade name ELASTIPRO™ 4013 and has a basis weight of about 50 gsm. The nonwovens were cut into rectangles having a stretch direction dimension of 95 mm and a second direction dimension of 141 mm. The film was cut into a rectangle having a stretch direction dimension and, in its stretched state, the width grew by about 4 mm due to set. The second nonwoven was then applied such that the film is sandwiched between the first and second nonwoven. While the film was stretched as described, the laminate was ultrasonically bonded. The bond pattern shown in FIG. 4A was used. Each nub has a bond area of 0.49 mm².

Comparative Example 2A is the same as Comparative Example 1 except the elastomeric film is available from EXTEN under the tradename EXTRETCH30 and has a basis weight of about 30 gsm.

Comparative Example 3A is the same as Comparative Example 1 except the elastomeric film is available from Tredegar Corp. under the tradename CEX802W and has a basis weight of about 50 gsm.

Inventive Examples 1B through 1H are each the same as Comparative Example 1A except while the film was stretched as described, the laminates were ultrasonically bonded using the bonding patterns shown in FIG. 4B through FIG. 4H respectively.

Inventive Examples 2B through 2H are each the same as Comparative Example 2A except while the film was stretched as described, the laminates were ultrasonically bonded using the bonding patterns shown in FIG. 4B through FIG. 4H respectively.

Inventive Examples 3B through 3H are each the same as Comparative Example 3A except while the film was stretched as described, the laminates were ultrasonically bonded using the bonding patterns shown in FIG. 4B through FIG. 4H respectively.

Table 1 below provides information regarding the bond dimensions and summaries which pattern is provided in each laminate.

TABLE 1

Figures 4A, 4B, 4C, 4D, 4E, 4F, 4G, 4H:
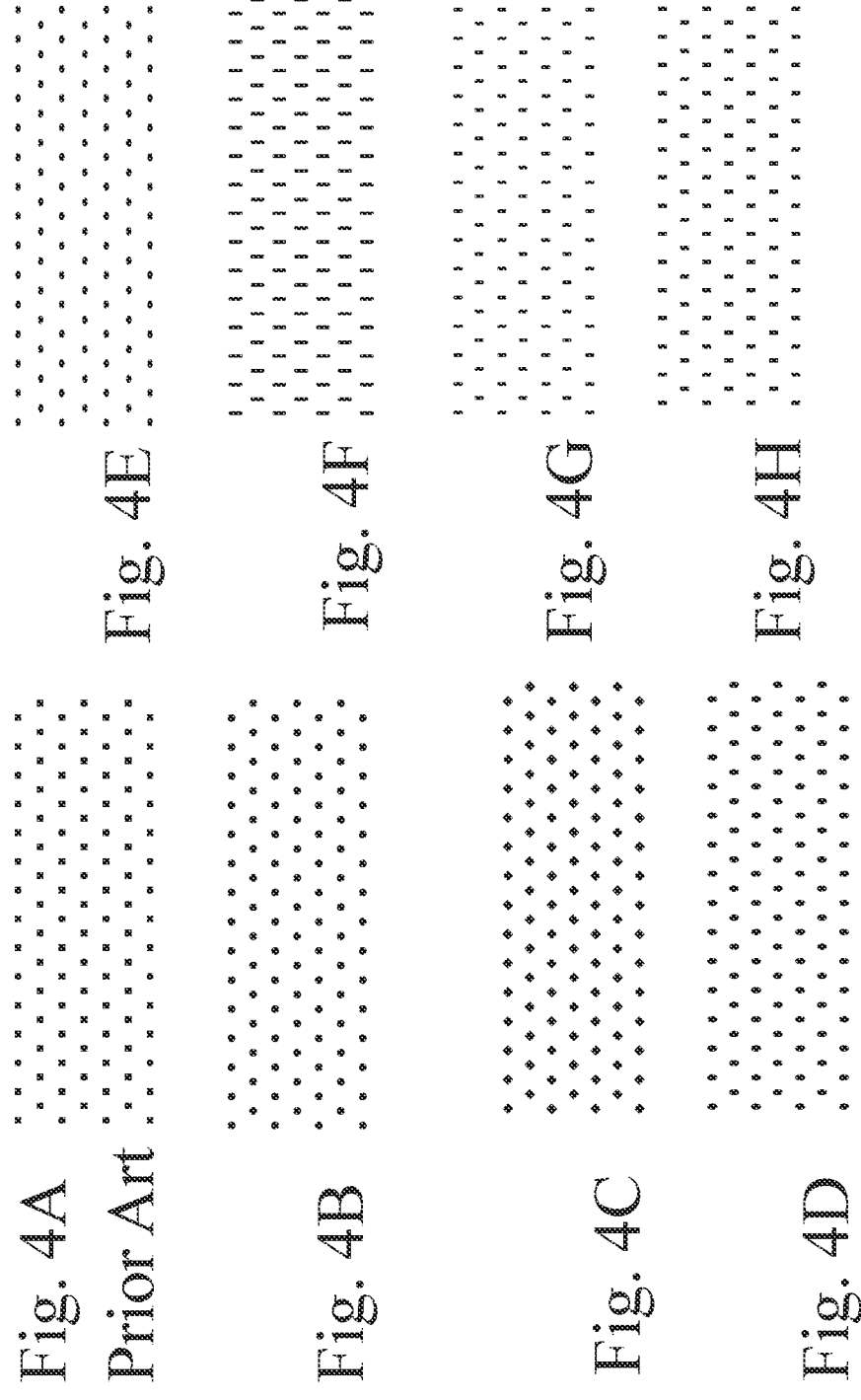
FIG. 4A is a schematic representation of an exemplary prior art bonding pattern.
FIGS. 4B-4H are schematic representations of exemplary bonding patterns according to nonlimiting embodiments of the present invention.

| Pattern | Bond shape | Second direction length (mm) | Stretch direction width (mm) | Aspect Ratio | Nub Bond Area (mm²) | Laminates with the Pattern |
|---|---|---|---|---|---|---|
| FIG. 4A | Square | 0.7 | 0.7 | 1 | 0.49 | Comparative Examples 1A-3A |
| FIG. 4B | Circle | 0.79 | 0.79 | 1 | 0.49 | Inventive Examples 1B, 2B and 3B |
| FIG. 4C | Diamond (Rotated Square) | 0.99 | 0.99 | 1 | 0.49 | Inventive Examples 1C, 2C and 3C |
| FIG. 4D | Ellipse Second direction | 1.12 | 0.56 | 2 | 0.49 | Inventive Examples 1D, 2D and 3D |
| FIG. 4E | Ellipse Stretch direction | 0.56 | 1.12 | 2 | 0.49 | Inventive Examples 1E, 2E and 3E |
| FIG. 4F | Rounded rectangle | 1.85 | 0.28 | 6.6 | 0.49 | Inventive Examples 1F, 2F and 3F |
| FIG. 4G | Rounded rectangle | 1.26 | 0.42 | 3 | 0.49 | Inventive Examples 1G, 2G and 3G |
| FIG. 4H | Rectangle | 1.2 | 0.4 | 3 | 0.49 | Inventive Examples 1H, 2H and 3H | of 44 mm and a second direction dimension of 140 mm. The laminate was assembled using an Ultrasonic Scanner, available from Branson Ultrasonics under tradename Branson 2000X and a bonding plate with the desired pattern. The film was stretched 130% strain (i.e., 44 mm stretched to about 103 mm, including an inelastic zone of 7 mm on each side)

Figure 5:
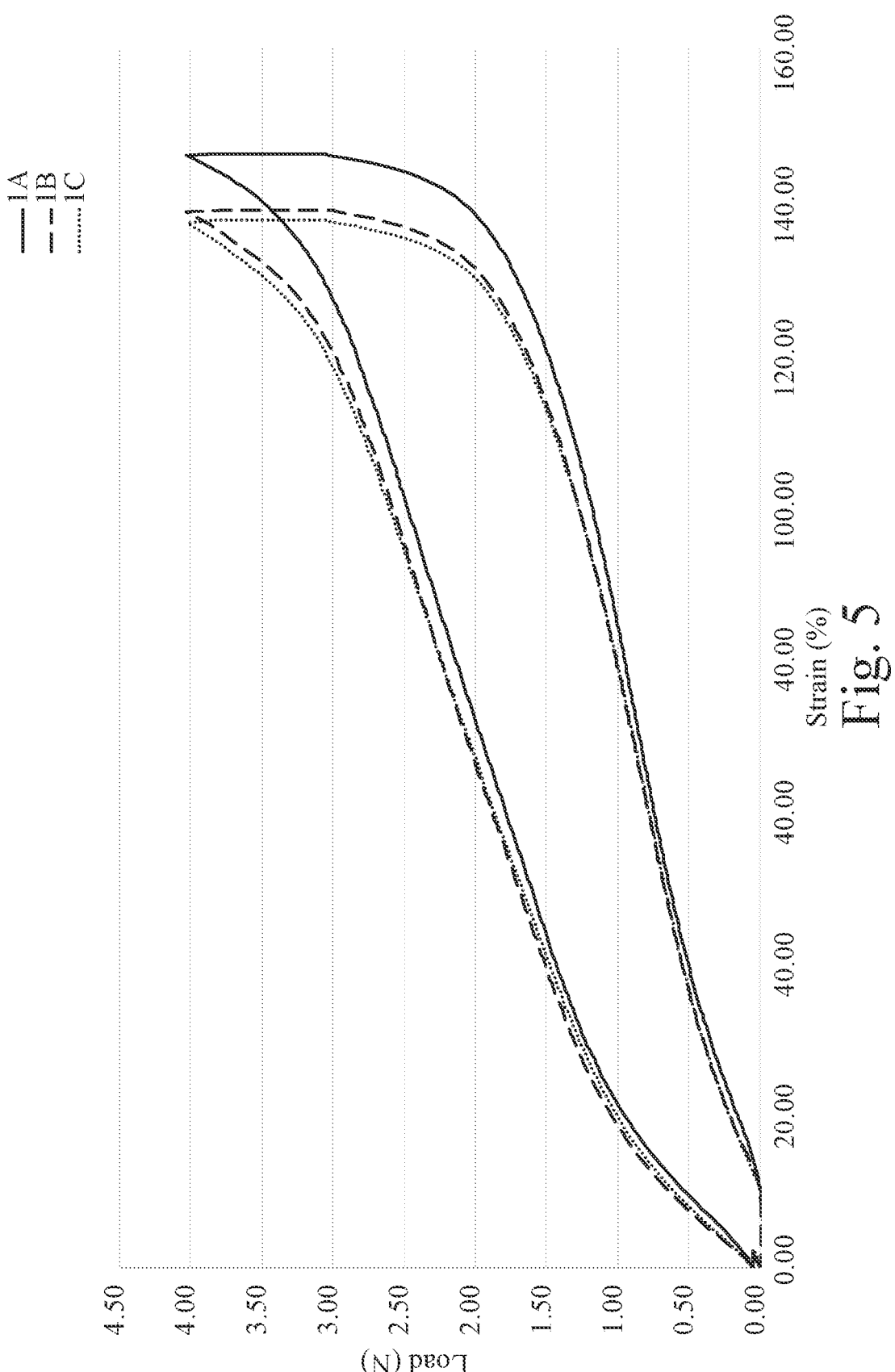
FIGS. 5-7 are chart showing the Load (N/in) versus strain (%) and related force curves for laminates in accordance with nonlimiting examples of the present invention.
Figure 6:
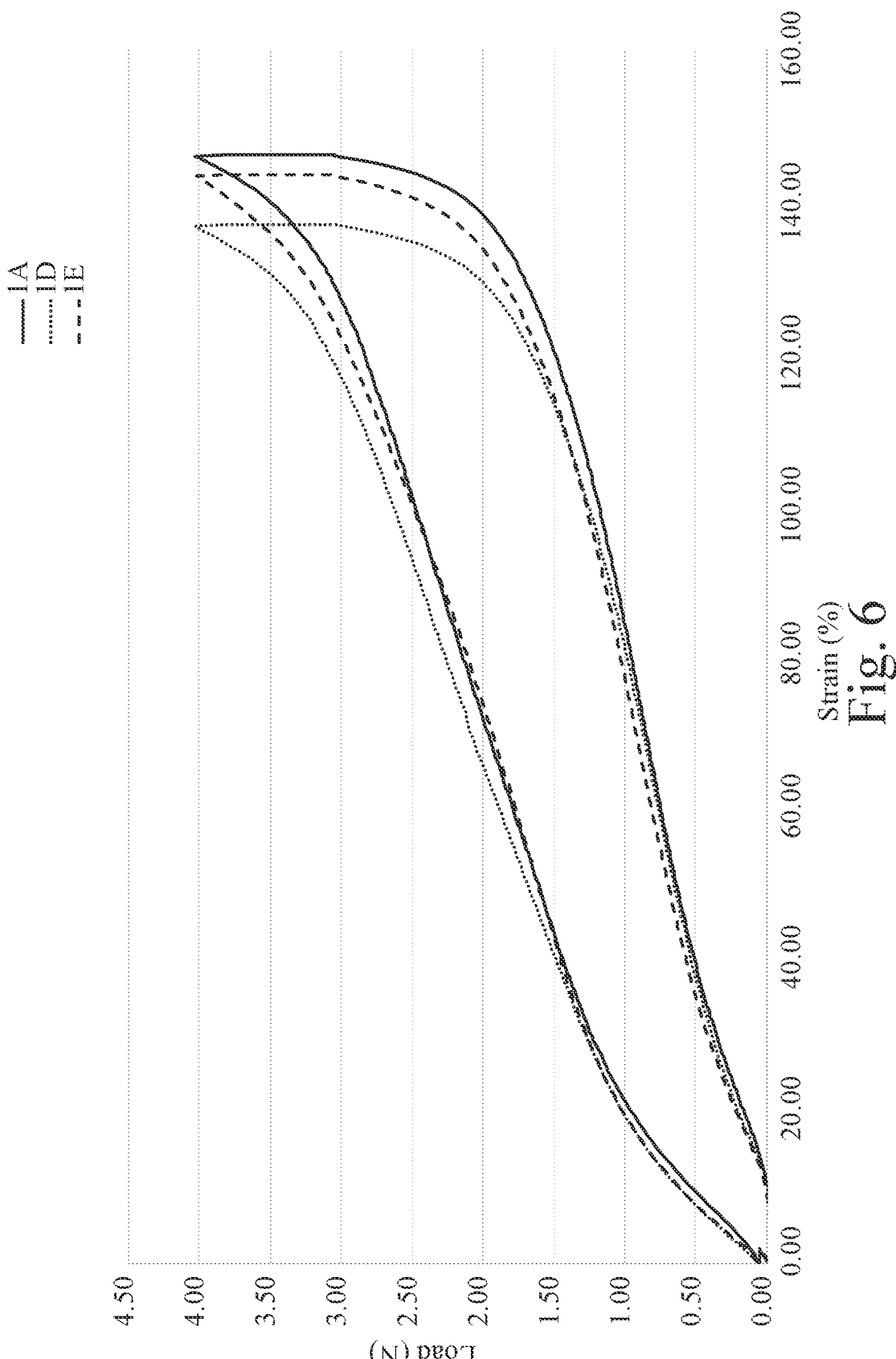
Figure 7:
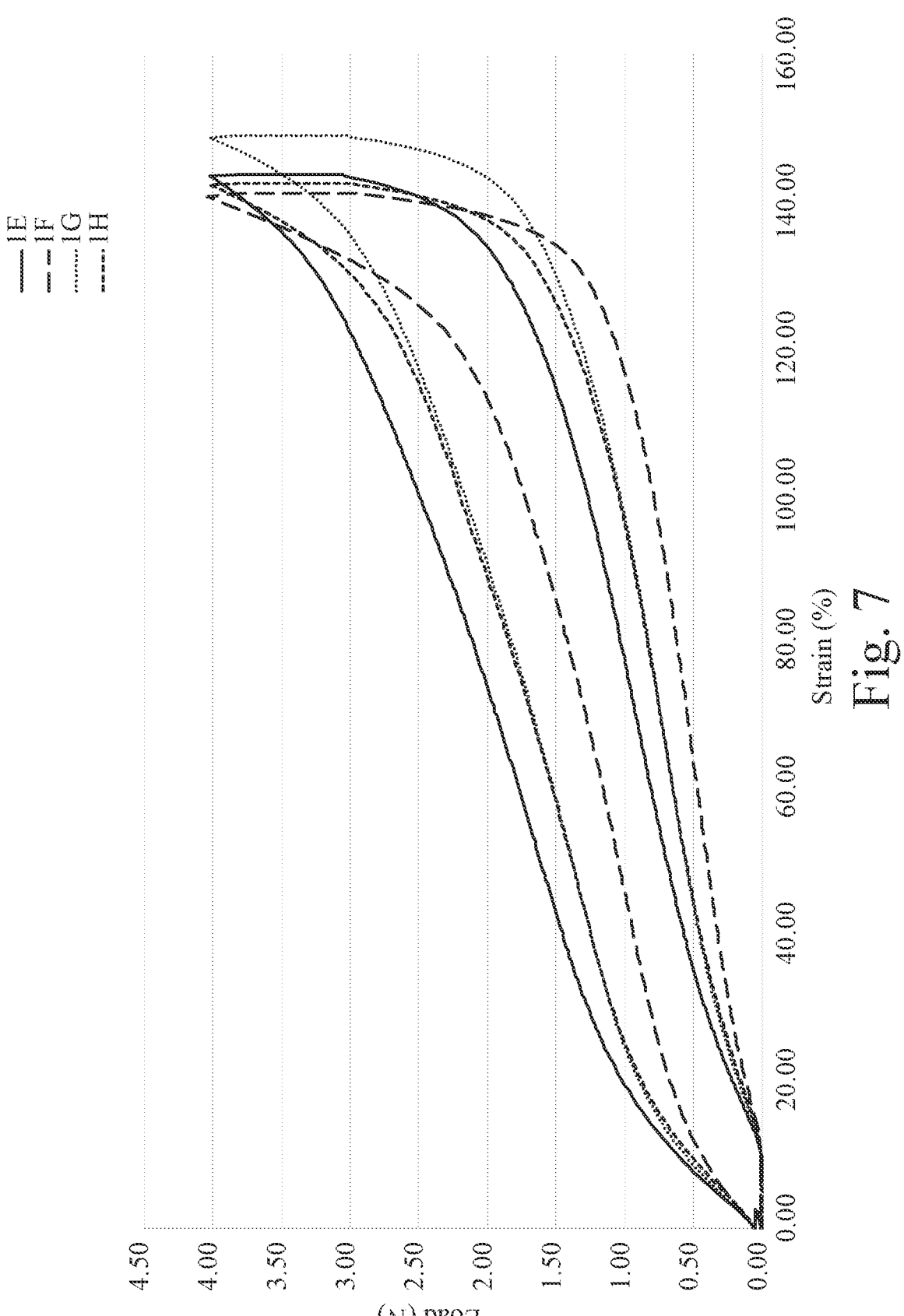

As exemplified in FIGS. 5-7, when holding the bond area consistent, the inventive bond geometries produced desirable strength, extensibility and resiliency while providing for flexibility in bond design. Further, inventive laminates provided improved tear resistance. The figures are charts of force loading and unloading curves for the various laminates. The force loading curve illustrates the amount of force required for the laminate to achieve a particular extension. Stated differently, the force loading curve relates to applied force during extension. The force loading curve is a proxy for ease of extending a laminate during product application or otherwise. The force unloading curve illustrates the amount of force the laminate can apply to the wearer while returning to its initial state (or as close to its initial state as possible). The force unloading curve is a proxy for the laminates durability when it is worn, after application. The closer that a force loading curve is to a force unloading curve (i.e., the lower the Hysteresis Ratio), the more resilient the laminate is. Typically, resilient laminates are more expensive due to the more expensive materials required. However, the inventors have surprisingly found that resilient laminates can be produced with lower cost, high modulus materials using the inventive bond patterns and teachings disclosed herein. As noted above, in some embodiments, it may be desirable to have a higher unload force even if a lower Hysteresis Ratio (3 or less) cannot be achieved.

FIG. 5 compares Comparative Example 1A (having the pattern shown in FIG. 4A) and Inventive Examples 1B and 1C (having the patterns in FIGS. 4B and 4C respectively). The chart illustrates that the patterns in FIGS. 4B and 4C can approximate the force profile and resiliency of the known pattern, while providing variability in bond design. While the chart in FIG. 5 depicts laminates in examples 1A-1C, the same trend is shown in the data of examples 2A-2C and 3A-3C.

FIG. 6 compares Comparative Example 1A and Inventive Examples 1D through 1E. The chart illustrates that the pattern in FIG. 4D can approximate the force profile and resiliency of the known pattern, while providing flexibility in bond design. Moreover, the chart illustrates that the pattern in FIG. 4E performs better than the known pattern. Indeed, while the pattern approximates the loading curve of the comparative example, the pattern provides a better return curve. In comparing D and E, it can be seen that the bond dimensions are the same, however, the bonds oriented in the stretch direction (pattern in FIG. 4E) provide a better, higher return force. Indeed, as shown in the Tables below, the pattern in FIG. 4E consistently has a higher return force.

FIG. 7 compares Inventive Examples 1E through 1H. As shown in the Tables below, the patterns in FIGS. 4F through 4G generally have a lower Load Force at 50% and lower Unload Force at 50% than Comparative Example 1A. Indeed, the force loading curves are generally lower than that of the comparative example as can be shown by comparing FIGS. 6 and 7. Further, FIG. 7 illustrates that the patterns in FIGS. 4F through 4H provide lower force loading curves than the comparative example, indicating lower forces are necessary to achieve the same extension, for at least a portion of the loading curve. Further, the charts demonstrate the laminate having second direction oriented bonds with a major dimension of greater than 1.2 mm has reduced performance versus the comparative example. Indeed, the more bonds are oriented in the second direction, the greater the force reduction. While the chart in FIG. 7 depicts laminate in examples 1E-1H, the same trend is shown in the data of examples 2E-2H and 3E-3H.

Table 2 illustrates the Hysteresis Ratio of the examples, as determined by the Hysteresis Test Method herein.

TABLE 2

| Laminates with ELASTIPRO 4013 Film | | | | | | | |
|---|---|---|---|---|---|---|---|
| Bond | Nub shape | | Hysteresis | Load Force at 50% | | Unload Force at 50% | |
| Pattern | description | Example | Ratio | N/in | MPa | N/in | MPa |
| FIG. 4A | Square | Comparative Example 1A | 2.53 | 1.62 | 1.19 | 0.64 | 0.47 |
| FIG. 4B | Circle | Inventive Example 1B | 2.55 | 1.71 | 1.25 | 0.67 | 0.49 |
| FIG. 4C | Diamond | Inventive Example 1C | 2.51 | 1.68 | 1.23 | 0.67 | 0.49 |
| FIG. 4D | Ellipse Second direction | Inventive Example 1D | 2.60 | 1.69 | 1.24 | 0.65 | 0.48 |
| FIG. 4E | Ellipse Stretch Direction | Inventive Example 1E | 2.35 | 1.62 | 1.19 | 0.69 | 0.51 |
| FIG. 4F | Rounded rectangle | Inventive Example 1F | 2.63 | 1.05 | 0.77 | 0.4 | 0.29 |
| FIG. 4G | Rounded rectangle | Inventive Example 1G | 2.53 | 1.39 | 1.02 | 0.55 | 0.40 |
| FIG. 4H | Rectangle | Inventive Example 1H | 2.48 | 1.39 | 1.02 | 0.56 | 0.41 |

TABLE 3

| Laminates with EXTRETCH30 Film | | | | | | | |
|---|---|---|---|---|---|---|---|
| Bond | Nub shape | | Hysteresis | Load Force at 50% | | Unload Force at 50% | |
| Pattern | description | Example | Ratio | N/in | MPa | N/in | MPa |
| FIG. 4A | Square | Comparative Example 2A | 3.54 | 1.45 | 1.77 | 0.41 | 0.50 |
| FIG. 4B | Circle | Inventive Example 2B | 3.37 | 1.28 | 1.56 | 0.38 | 0.46 |

TABLE 3-continued

| Bond | Nub shape | | Hysteresis | Load Force at 50% | | Unload Force at 50% | |
|---|---|---|---|---|---|---|---|
| | | | | Laminates with EXTRETCH30 Film | | | |
| Pattern | description | Example | Ratio | N/in | MPa | N/in | MPa |
| FIG. 4C | Diamond | Inventive Example 2C | 3.33 | 1.2 | 1.46 | 0.36 | 0.44 |
| FIG. 4D | Ellipse Second direction | Inventive Example 2D | Not measured | Not measured | Not measured | Not measured | Not measured |
| FIG. 4E | Ellipse Stretch Direction | Inventive Example 2E | 3.31 | 1.39 | 1.70 | 0.42 | 0.51 |
| FIG. 4F | Rounded rectangle | Inventive Example 2F | 3.52 | 0.95 | 1.16 | 0.27 | 0.33 |
| FIG. 4G | Rounded rectangle | Inventive Example 2G | 2.97 | 1.13 | 1.38 | 0.38 | 0.46 |
| FIG. 4H | Rectangle | Inventive Example 2H | Not measured | Not measured | Not measured | Not measured | Not measured |

TABLE 4

| Bond | Nub shape | | Hysteresis | Load Force at 50% | | Unload Force at 50% | |
|---|---|---|---|---|---|---|---|
| | | | | Laminates with CEX802W Film | | | |
| Pattern | description | Example | Ratio | N/in | MPa | N/in | MPa |
| FIG. 4A | Square | Comparative Example 3A | 2.39 | 1.34 | 0.98 | 0.56 | 0.41 |
| FIG. 4B | Circle | Inventive Example 3B | 2.37 | 1.35 | 0.99 | 0.57 | 0.42 |
| FIG. 4C | Diamond | Inventive Example 3C | 2.41 | 1.3 | 0.95 | 0.54 | 0.40 |
| FIG. 4D | Ellipse Second direction | Inventive Example 3D | 2.51 | 1.23 | 0.90 | 0.49 | 0.36 |
| FIG. 4E | Ellipse Stretch Direction | Inventive Example 3E | 2.23 | 1.38 | 1.01 | 0.62 | 0.45 |
| FIG. 4F | Rounded rectangle | Inventive Example 3F | 2.61 | 0.94 | 0.69 | 0.36 | 0.26 |
| FIG. 4G | Rounded rectangle | Inventive Example 3G | 2.37 | 1.21 | 0.89 | 0.51 | 0.37 |
| FIG. 4H | Rectangle | Inventive Example 3H | 2.55 | 1.2 | 0.88 | 0.47 | 0.34 |

The laminate examples were also tested under the Force Drop Test Method herein.

Inventive Examples 1E, 2E and 3E (all of which comprise the pattern in FIG. 4E) showed no tearing after 8 hours of testing, while the remaining patterns had a Growth in Aperture of over 50% after 8 hours regardless of the film. As shown in Table 5 below, Inventive Examples 1-E, 2-E and 3-E also exhibited a 10-Hour Force Drop of 65% or less, more particularly of 60% or less. This further shows that under conditions that are representative of the wearing experience stretch orientated bonds can provide additional patterns and visual appearance improvements without compromising the fit/performance of the product.

TABLE 5

| Laminate with ELASTIPRO film | 10-Hour Force Drop | Growth in Aperture >50%? | Laminate EXTRETCH 30 film | 10-Hour Force Drop | Growth in Aperture >50%? | Laminate CEX802 film | Growth in Aperture >50%? | 10-Hour Force Drop |
|---|---|---|---|---|---|---|---|---|
| Comparative Example 1A | 56.7% | Yes | Comparative Example 2A | 76.6% | Yes | Comparative Example 3A | Yes | 53.8% |
| Inventive Example 1-B | 65.0% | Yes | Inventive Example 2-B | 75.0% | Yes | Inventive Example 3-B | Yes | 57.7% |
| Inventive Example 1-C | 71.0% | Yes | Inventive Example 2-C | 56.1% | Yes | Inventive Example 3-C | Yes | 58.5% |
| Inventive Example 1-D | 61.5% | Yes | Inventive Example 2-D | 53.7% | Yes | Inventive Example 3-D | Yes | 57.5% |
| Inventive Example 1-E | 56.1% | No | Inventive Example 2-E | 54.8% | No | Inventive Example 3-E | No | 57.0% |
| Inventive Example 1-F | 77.6% | Yes | Inventive Example 2-F | 67.0% | Yes | Inventive Example 3-F | Yes | 58.6% |

TABLE 5-continued

| Laminate with ELASTIPRO film | 10-Hour Force Drop | Growth in Aperture >50%? | Laminate EXTRETCH 30 film | 10-Hour Force Drop | Growth in Aperture >50%? | Laminate CEX802 film | Growth in Aperture >50%? | 10-Hour Force Drop |
|---|---|---|---|---|---|---|---|---|
| Inventive Example 1-G | 57.2% | Yes | Inventive Example 2-G | 67.4% | Yes | Inventive Example 3-G | Yes | 43.7% |
| Inventive Example 1-H | 60.9% | Yes | Inventive Example 2-H | 57.7% | Yes | Inventive Example 3-H | Yes | 54.9% |

Article Comprising Laminate

Figure 8:
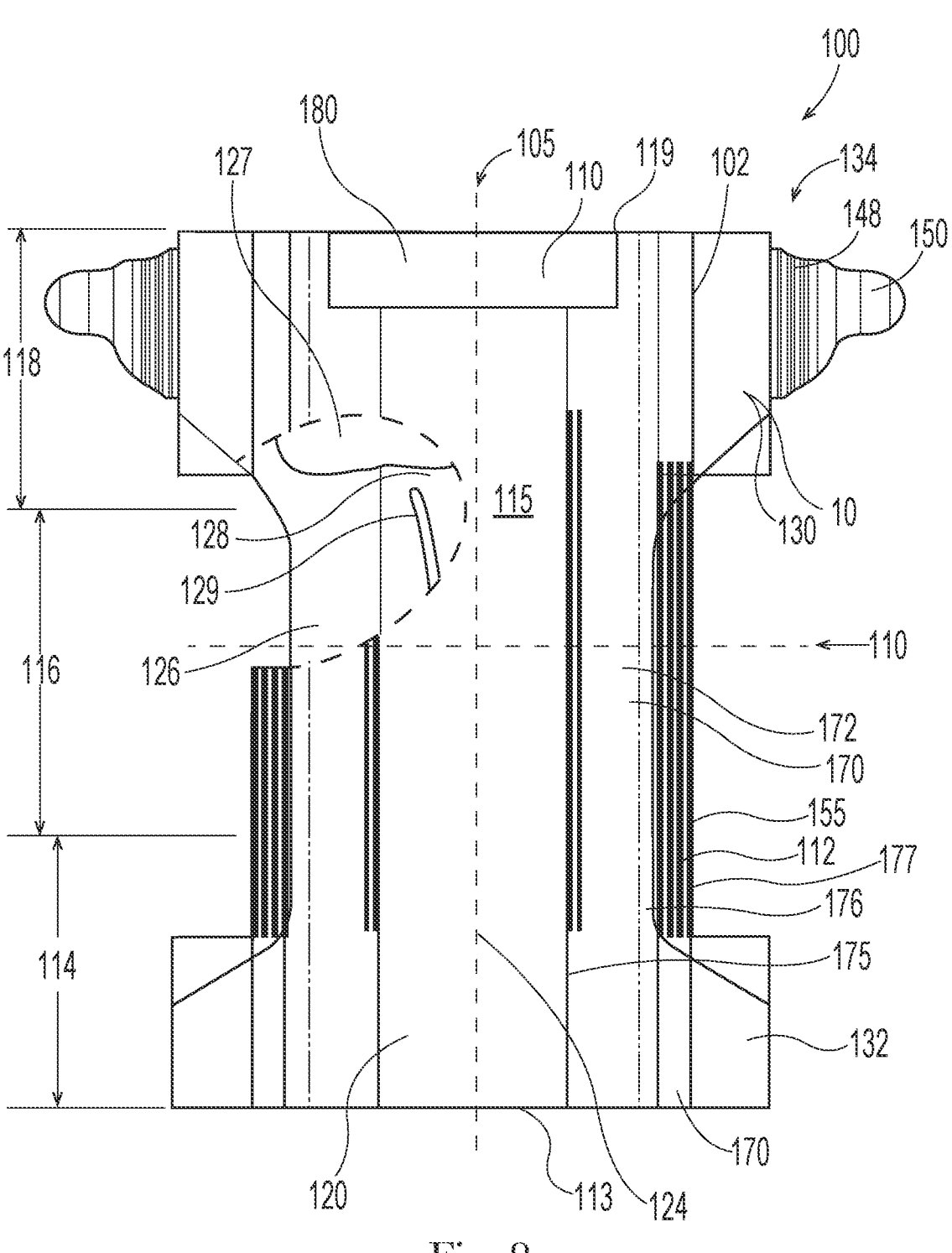
FIG. 8 is schematic plan view of an exemplary absorbent article according to one nonlimiting embodiment of the present invention. The absorbent article is shown in a flat, uncontracted state.

Turning to FIG. 8, a laminate 10 of the present invention may be incorporated into an absorbent article 100, such as a disposable absorbent article. The laminate may be attached to one or more layers of the chassis 120 by a chassis attachment bond 102. The chassis attachment bond may comprise ultrasonic bonds, adhesive bonds, mechanical bonds or combinations thereof.

FIG. 8 is a plan view of an exemplary, non-limiting embodiment of an absorbent article 100 of the present invention in a flat, uncontracted state. The body-facing surface 115 of the absorbent article 100 is facing the viewer. The absorbent article 100 includes a longitudinal centerline 105 and a lateral centerline 110.

The absorbent article 100 comprises a chassis 120. The absorbent article 100 and chassis 120 are shown to have a first waist region 114, a second waist region 118 opposed to the first waist region 114, and a crotch region 116 located between the first waist region 114 and the second waist region 118. The waist regions 114 and 118 generally comprise those portions of the absorbent article which, when worn, encircle the waist of the wearer. The waist regions 114 and 118 may include elastic members 155 such that they gather about the waist of the wearer to provide improved fit and containment. The crotch region 116 is the portion of the absorbent article which, when the absorbent article is worn, is generally positioned between the legs of the wearer.

The outer periphery of the chassis 120 is defined by longitudinal edges 112 and waist edges (first waist edge 113 in first waist region 114 and second waist edge 119 in second waist region 118). The chassis 120 may have opposing longitudinal edges 112 that are oriented generally parallel to the longitudinal centerline 105. However, for better fit, longitudinal edges 112 may be curved or angled to produce, for example, an "hourglass" shape article when viewed in a plan view as shown in FIG. 8. The chassis 120 may have opposing lateral edges 113, 119 (i.e., the first waist edge 113 and second waist edge 119) that are oriented generally parallel to the lateral centerline 110.

The chassis 120 may comprise a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126. In some embodiments, an acquisition-distribution system 127 is disposed between the topsheet 126 and the absorbent core 128.

In certain embodiments, the chassis 120 comprises the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151, 092; 5,221,274; 5,554,145; 5,569,234; 5,580,411; and 6,004, 306.

Components of the disposable absorbent article can at least partially be comprised of bio-sourced content as described in U.S. Pat. Pub. Nos. 2007/0219521 A1, 2011/ 0139658 A1, 2011/0139657 A1, 2011/0152812 A1, and 2011/0139659 A1. These components include, but are not limited to, topsheets, backsheet films, backsheet nonwovens, ears/ear laminates, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

The laminate 10 of the present invention may be form or be a portion of one or more components of the article, including but not limited to the ear, waist features, belts and combinations thereof.

Topsheet

The topsheet 124 is generally a portion of the absorbent article 100 that may be positioned at least in partial contact or close proximity to a wearer. Suitable topsheets 124 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 124 is generally supple, soft feeling, and non-irritating to a wearer's skin. Generally, at least a portion of the topsheet 124 is liquid pervious, permitting liquid to readily penetrate through the thickness of the topsheet 124. The topsheet 124 may be apertured. The topsheet may be apertured by overbonding a material and then rupturing the overbonds through ring rolling, such as disclosed in U.S. Pat. No. 5,628,097.

Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core

The absorbent core 128 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 129, wherein said channels are substantially free of absorbent particulate polymer material. The channels 129 may extend longitudinally or laterally. The absorbent core may further comprise two or more channels. The channels may be straight, curvilinear, angled or any workable combination thereof. In nonlimiting examples, two channels are symmetrically disposed about the longitudinal axis.

Backsheet

The backsheet 126 is generally positioned such that it may be at least a portion of the garment-facing surface of the absorbent article 100. The backsheet 126 may be joined to portions of the topsheet 124, the absorbent core 128, and/or any other layers of the absorbent article by any attachment methods known to those of skill in the art. Backsheet 126 may be designed to prevent the exudates absorbed by and contained within the absorbent article 100 from soiling articles that may contact the absorbent article 100, such as bed sheets and undergarments. In certain embodiments, the backsheet 126 is substantially water-impermeable. The backsheet may, for example, be or comprise a thin plastic film, such as a thermoplastic film having a thickness of about 0.012 mm to about 0.051 mm Other suitable backsheet materials may include breathable materials which permit vapors to escape from the absorbent article, while still preventing, or at least inhibiting, bodily exudates from passing through the backsheet.

Backsheet 126 may also consist of more than one layer. The backsheet 126 may comprise an outer cover and an inner layer. The outer cover material 40 may comprise a bond pattern, apertures, and/or three-dimensional features. The outer cover material 40 may be a nonwoven material, such as a hydroentangled nonwoven material. The inner layer may be made of a substantially liquid-impermeable film, such as a polymeric film. The outer cover and an inner layer may be joined together by adhesive or any other suitable material or method.

Ears/Fasteners

The absorbent article 100 may include one or more ears 130, including for example front ears 132 disposed in the first waist region and/or back ears 134 disposed in the second waist region. The ears 130 may be integral with the chassis or discrete elements joined to the chassis 120 at a chassis attachment bond 102, which may join one or more layers of the ear to the chassis. The ears 130 may be extensible or elastic. The ears 130 may be formed from one or more nonwoven webs, woven webs, knitted fabrics, polymeric and elastomeric films, apertured films, sponges, foams, scrims, or combinations and/or laminates of any the foregoing.

In some embodiments, the ear 130 may include elastomers, such that the ear is stretchable. In certain embodiments, the ears 130 may be formed of a stretch laminate such as a nonwoven/elastomeric material laminate or a nonwoven/elastomeric material/nonwoven laminate, which also results in the ear being stretchable. The ear 120 may be extensible in the lateral direction of the article. In some embodiments, the ear is elastic in the lateral direction. In further embodiments, the ear 130 may extend more in the lateral direction than in the longitudinal direction. Alternatively, the ear may extend more in the longitudinal direction than in the lateral direction. In certain nonlimiting examples, the ear may include one or more inelastic regions along with a separate elastic region.

In some embodiments, the ear comprises a laminate of one or more nonwovens and one or more elastic materials, such as the laminate 10 having any of the features or laminate layers described herein with respect to laminates of the present invention.

Any suitable nonwoven may be used in an ear 130. Suitable nonwovens may comprise a basis weight of at least about 8 gsm, or less than about 30 gsm, or about 17 gsm or less, or from about 10 gsm to about 17 gsm, reciting for said range every 1 increment therein. Typically, lower basis weight nonwovens reduce an ear's overall strength. However, the inventors have discovered ears designed according to the principles herein can obtain high strength despite lower basis weight nonwovens. Where the ear 130 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

The ear may comprise an ultrasonically bonded ear as is disclosed for example in U.S. patent application Ser. No. 15/674,559. The ear may be a gathered laminate 24. Alternatively, the ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example.

The ear may be joined to the chassis at a chassis attachment bond 102. In some nonlimiting examples, the chassis attachment bond is located in an inelastic region of the ear.

The absorbent article 100 may also include a fastening system 148. When fastened, the fastening system 148 interconnects the first waist region 116 and the rear waist region 118 resulting in a waist circumference that may encircle the wearer during wear of the absorbent article 100. The fastening system 148 may comprise a fastening elements 150 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 148 and/or the element 150 is foldable.

The fastening system 148 may be joined to any suitable portion of the article 100 by any suitable means. The fastening system may be joined to the ear between layers.

Leg Gasketing System

The absorbent article 100 may comprise a leg gasketing system 170 attached to the chassis 120, which may comprise one or more cuffs. The leg gasketing system may comprise a pair of barrier leg cuffs 172. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 comprises a folded edge. The barrier leg cuffs 172 extend at least partially between the front waist edge 113 and the rear waist edge 119 of the absorbent article on opposite sides of the longitudinal centerline 105 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may comprise one, two or more elastic elements 155 close to the free terminal edge 175 to provide a better seal.

In addition to the barrier leg cuffs 172, the article may comprise gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may comprise a proximal edge and a free terminal edge 177. The free terminal edge 177 may comprise a folded edge. Each gasketing cuff may comprise one or more elastic elements 155 in the chassis of the absorbent article between the topsheet 124 and backsheet 126 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, Ser. No. 14/077,708; U.S. Pat. Nos. 8,939,957; 3,860, 003; 7,435,243; 8,062,279.

Elastic Waist Feature

The absorbent article 100 may comprise at least one elastic waist feature 180 that helps to provide improved fit and containment, as shown in FIG. 8. The elastic waist feature 180 is generally intended to expand and contract to dynamically fit the wearer's waist. Elasticized waist features include waistbands, waist cuffs having pockets formed from a portion of the waist feature 180 that is unattached from the chassis 120, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 120 in the first waist region 114 and/or in the second waist region 118. The waist feature can be used in conjunction with the ear 130 to provide desirable stretch and flexibility for proper fit of the article on the wearer. The waist feature may comprise a laminate 10 having any of the features described herein with respect to laminates. The waist feature may be extensible or elastic in the lateral and/or longitudinal directions. In some embodiments, the waist feature 180 comprises a belt 220.

Adult or Baby Pant Absorbent Articles

Figures 9A, 9B:
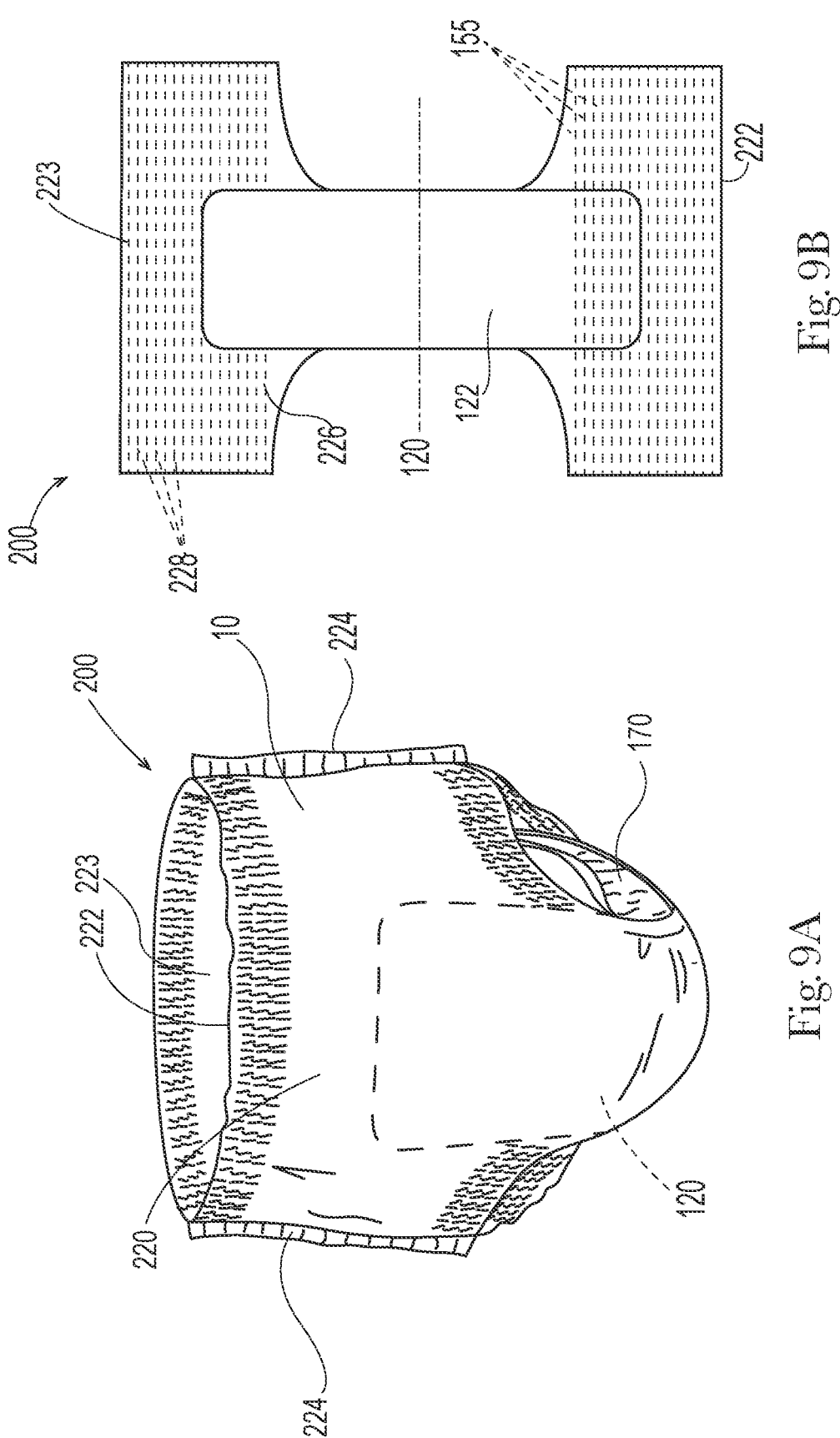
FIG. 9A is a schematic perspective view of an exemplary embodiment of an absorbent pant as detailed herein.
FIG. 9B is a schematic plan view of an exemplary embodiment of an absorbent pant precursor structure, prior to joining of the front and rear sections of the belt.

In some embodiments, the article 100 may comprise an absorbent pant 200 as shown in FIGS. 9A and 9B The absorbent pant may comprise include a chassis 122, a belt 220 to be positioned about the wearer's waist, and optionally a leg gasketing system 170. FIG. 9B depicts an exemplary precursor structure of the pant in FIG. 9A, in an open configuration laid out flat and stretched out laterally against elastic-induced contraction. In the final assembly of the pant, the front belt portion 222 is joined to rear belt portion 223 at seams 224, which may be permanent or refastenable. To form the pant 200, the precursor structure may be folded at or about lateral centerline 110 with the topsheet 124 facing inward, and the longitudinal edges of the front 222 and rear 223 belt portions may be joined at seams 224, forming a pant structure having leg openings, front waist edge and rear waist edge. In this way, the pant 200 may comprise a pre-formed, continuous waist opening and pre-formed, continuous leg openings for the wearer at the time of donning the pant 200.

The front and rear belt portions 222, 223 may be the outermost structures forming the front and rear regions of a pant 200. The pant may include an outer wrap 226 wrapping the entirety of the front, crotch and rear regions, and forming an outermost pant-shaped structure. In some embodiments, the outer cover of the backsheet forms the outer wrap. An outer wrap 226 may be formed of one or more sections of nonwoven web and may be cut to a profile providing suitably tailored leg opening edge profiles as desired.

A belt 220 may comprise the laminate 10 of the present invention, having any of the afore-described features including one or more nonwoven layers and one or more elastomeric layers. The laminate layers may be joined by ultrasonic bonding.

According to some nonlimiting examples, the nonwoven used for a belt portion may include a material that provides good recovery when external pressure is applied and removed.

Elastomeric layers of waist features, such as belt portions, may comprise one or more elastic members 155. The elastic members 155 may be elastomeric fibers, such as LYCRA® fibers available from INVISTA of Wichita, Kans., in various decitex levels. The elastic members 155 may also comprise any heat shrinkable elastic material as is well known in the art. Other suitable elastics can be made various other materials including but not limited to: rubbers, styrene ethylbutylene styrene, styrene ethylene propylene styrene, styrene ethylene propylene styrene, styrene butadiene styrene, styrene isoprene styrene, polyolefin elastomers, elastomeric polyurethanes, and other elastomeric materials known in the art, and combinations thereof. In some nonlimiting examples, the elastic members may be extruded strand elastics with any number of strands (or filaments). In some embodiments, the elastic members can have a decitex ranging from 50 to 2000, or any integer value for any decitex value in this range. However, the skilled person may select the appropriate decitex based on the desired contraction and other principles discussed herein. In further embodiments, the elastic members may be in a form of film. Examples of films have been described in prior patent applications (see, for example, U.S. Pat. App. Pub. No. 2010/0040826). The film may be created with a variety of resins combined in at least one of several sublayers, the latter providing different benefits to the film.

In addition, elastic members 155 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

Layers of a waist feature (e.g., belt portion) and/or chassis 120 may be joined together about elastic strands 155 by adhesive deposited between the layers, by thermal bonds, by compression bonds, or by a combination thereof. In other examples, the one or more elastic members may be strips or a section of film formed of elastomeric material. Where the elastic member is elongate, it may be desirable that the longer dimension be laterally oriented, or even substantially aligned with the lateral direction, as strands 155 are depicted in FIG. 9B for example.

A belt portion or other form of waist feature may comprise at least 3 waist elastic members, at least 5 elastic members, at least 10 waist elastic members, or at least 15 waist elastic members, or from about 2 to about 35 waist elastic members, or from about 5 to about 25 waist elastic members, reciting for each range every 1 increment therein.

In one embodiment, adjacent elastic members 155 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist feature. For example, the spacing between adjacent elastic members could uniformly be 7 mm or there could be variable spacing (i.e., two adjacent elastic members are separated by 3 mm, another two are separated by 6.5 mm, etc.).

During manufacture of the waist feature, the elastic members 155 may be pre-strained by a desired amount as they are being incorporated into the waist feature. Upon subsequent relaxation of the waist feature, the elastic members will contract laterally toward their unstrained lengths. This may cause layers of the waist feature to gather and form ruffles or rugosities having ridges and valleys generally transverse to the lengths of the elastic members 155, and extending in the z-direction.

In further embodiments, to adhere the components of the waist feature laminate, the elastic members may be individually coated with adhesive ("strand coated") prior to incorporation into the waist laminate. Various coating methods and techniques, including strand coating methods and techniques, are shown for example in U.S. Pat. Nos. 5,340, 648; 5,501,756; 5,507,909; 6,077,375; 6,200,635; 6,235, 137; 6,361,634; 6,561,430; 6,520,237; 6,582,518; 6,610, 161; 6,613,146, 6,652,693, 6,719,846 and 6,737,102. The adhesive used may be a hot-melt type adhesive having elasticity and flexibility making it suitable for attaching pre-strained elastic materials to substrates, such as OMNIMELT BLOCKS 22 H2401F, or ZEROCREEP brands such as AVANCÉ, available from Bostik, Inc., Wauwatosa, Wis.

In certain embodiments, corners of the front and/or rear belt portion may be trimmed off as suggested in FIG. 9B. The corners may be trimmed off along straight lines, or may be trimmed off along trim paths that are curved and either concave or convex with respect to the remaining area of the belt portion, as may be desired to impart a particular curved leg edge profile. In conjunction with such trimming and the configuration of elastic strands described above, it may be desired to impart bonding between layers along edges of the respective belt portion 222, 223. Such bonding may serve to prevent any separation of the layers along edges that may contribute to creating a ragged appearance, and may also help the rear belt portion more effectively draw inward laterally toward the central chassis 120, under the contractive force of the elastic strands below seams 224. Bonding may be effected by mechanical/compression bonds as described in, for example, U.S. Pat. Nos. 4,854,984 and 4,919,738, by thermal bonds or welds, or by deposits of adhesive between layers. In nonlimiting examples, such bonding may form a pattern along edges. Such bonding may be supplemental to any bonding between layers generally holding the respective belt portion 222, 223 together as a laminate structure.

Side seams 224 may be permanent or refastenable. Permanent seams may be formed between the front belt portion and the rear belt portion by any bonding mechanism wherein the front and rear belt portions may not be forcibly separated without substantial damage to one or both of the front and rear belt portions, or without any included mechanism by which substantial reattachment or refastening may be effected. Bonding forming permanent seams may include compression bonding, thermal bonding/welds, ultrasonic bonding or adhesive bonding. Refastenable seams may be formed between the front belt portion and the rear belt portion by any mechanism configured to permit substantially non-destructive forcible separation of the front and rear belt portions, and subsequent substantial reattachment or refastening at the same locations. One example of such mechanism is a hook-and-loop fastening system, for example, a VELCRO fastening system. A suitably sized and shaped hooks component may be bonded to one of the front or rear belt portions along the longitudinal edges thereof, and a suitably sized and shaped loops component may be bonded to the other of the front or rear belt portions along the longitudinal edges thereof, in positions in which they may be brought together and engaged to form seams 224. Examples are depicted in U.S. Pat. App. Ser. Nos. 61/787, 416; 61/787,332; 61/666,065.

Exemplary belt and absorbent pant constructions are disclosed in U.S. patent application Ser. Nos. 14/598,783 and 14/032,595.

Package

The absorbent articles 100 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 10:
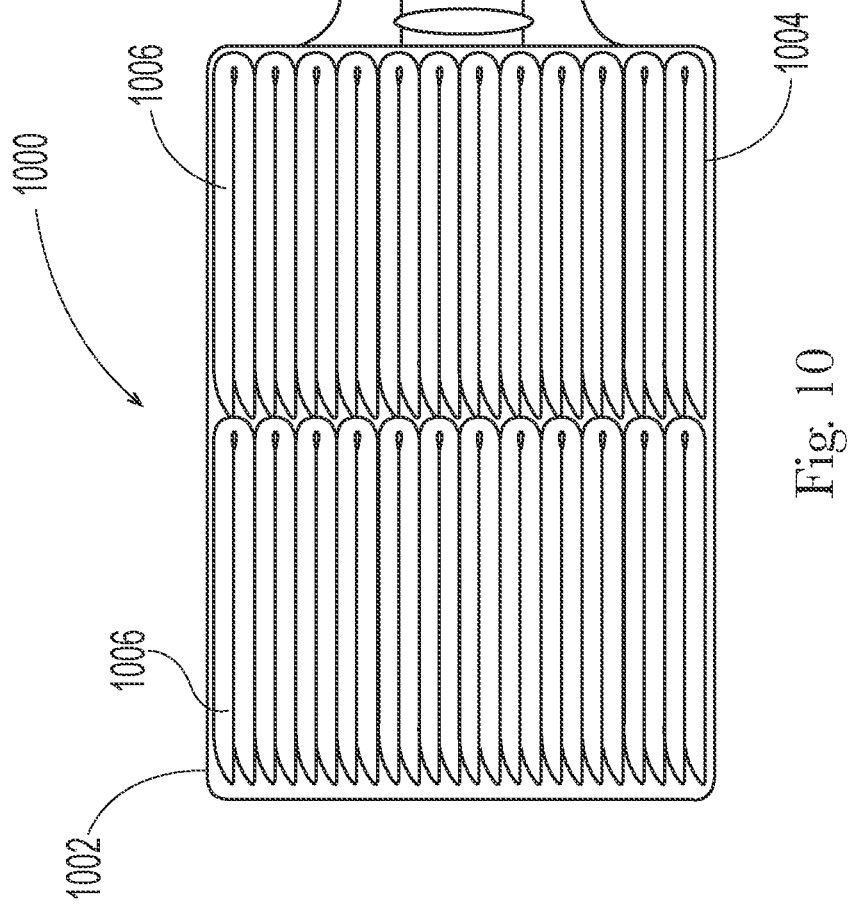
FIG. 10 is a schematic perspective view of a package in accordance with one embodiment of the present invention.

FIG. 10 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Test Methods
Sample Preparation

Unless otherwise specified in the specific methods below, samples are cut are prepared from the laminate or component as follows. For laminates/components having one bond pattern: A sample of the desired size (as prescribed in the method) is cut from the bond pattern area in the elastic region. If the available bond pattern area and/or elastic region is smaller than what is prescribed for the Hysteresis and 10-Hour Force Drop/Growth in Aperture Test Methods, then a sample as small as 10 mm wide (in the dimension perpendicular to the stretch direction) by 10 mm long (in the stretch direction) can be used. For laminates/components having more than one pattern: identity one bond pattern of interest (i.e., uniform bond pattern) in the elastic region. If the available bond pattern area is smaller than what is prescribed for the Hysteresis and 10-Hour Force Drop/Growth in Aperture Test Methods, then a sample as small as 10 mm wide (in the dimension perpendicular to the stretch direction) by 10 mm long (in the stretch direction) can be used. Care should be taken that gage length is kept the same as the width of the sample, and test strain rate is kept the same as prescribed in the methods.

Basis Weight

A sample of at least 1 cm² is used to measure basis weight from the uniform bond pattern area. Sample is weighed to within ±0.1 milligram using a digital balance. Sample length and width are measured using digital Vernier calipers or equivalent to within ±0.1 mm. All testing is conducted at 22±2° C. and 50±10% relative humidity. Basis weight is calculated using equation below.

26

$$\text{Basis Weight}\left(\frac{g}{m^2}\right)= \frac{(\text{Weight of the sample in grams})}{(\text{Length of the sample in meter})(\text{Width of the sample in meter})}$$

10-Hour Force Drop/Growth in Aperture Test Method

The purpose of this test is to measure the "10-Hour Force Drop" and "Growth in Aperture" for a laminate sample. This test provides information on how well the laminate secures an article to a wearer, i.e., product fit during use, when the laminate is held at 37.8° C. and an engineering strain of 100%.

Figures 11, 12:
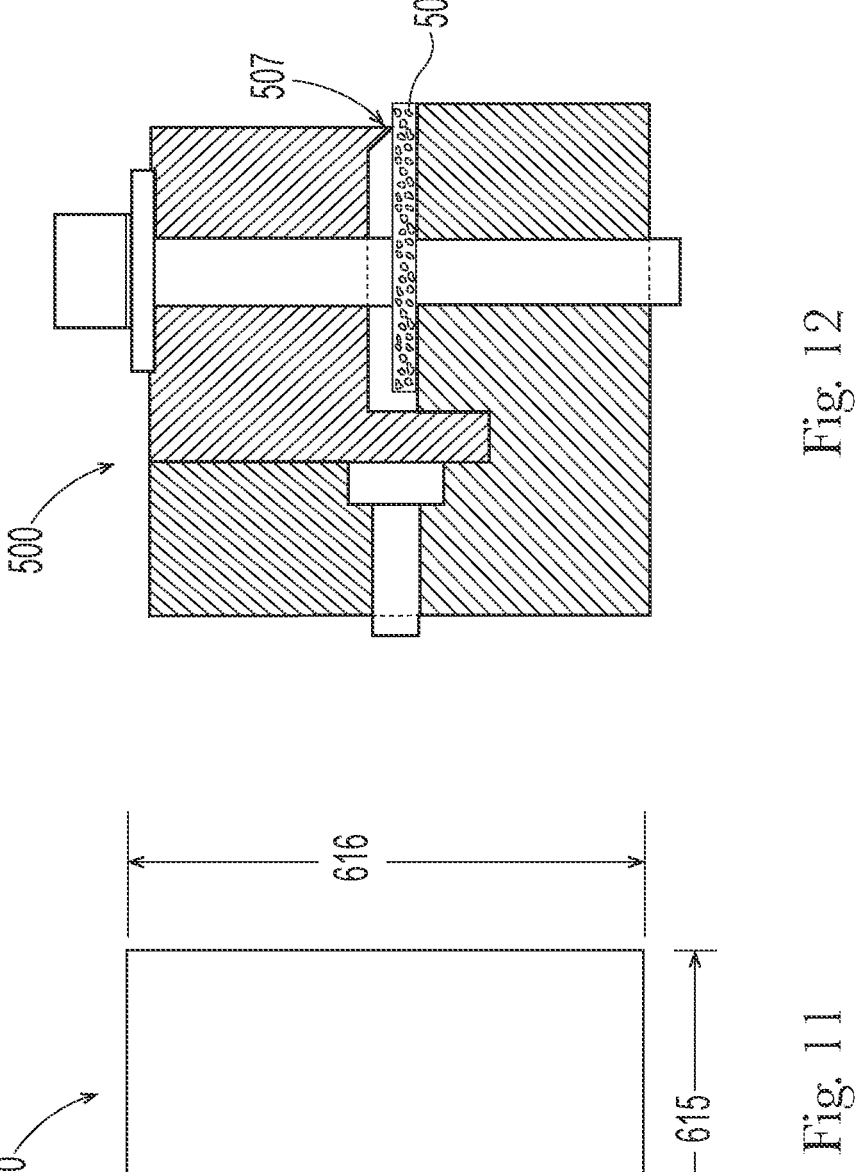
FIG. 11 is a schematic plan view of an exemplary sample for use in the 10-Hour Force Drop/Growth in Aperture Test Method herein.
FIG. 12 is a schematic, side elevation view of a grip suitable for use in the 10-Hour Force Drop/Growth in Aperture Test Method herein.

Setup
Gauge Length: 25.4 mm
Sample Width: 25.4 mm
Testing Temperature: 37.8° C.
Applied engineering strain: 100% (i.e. apply and hold 25.4 mm of displacement.)
Direction of applied deformation: the stretch direction of the laminate during normal use of the article Sample Preparation FIG. 11 is provided to illustrate particular aspects of the sample preparation. On a cutting mat, the laminate material is sandwiched between sheets of photocopier paper. A sharp, X-ACTO brand knife and straight edge are used to prepare the samples 600. The sample is cut from the uniform bond pattern area of the elastic region. A sample 600 is cut such that it has a width 615 of 25.4 mm and a length 616 that is suitable for loading the sample into the grips and is sufficient to provide a gauge length of 25.4 mm without undesirably interfering with the test. In this particular example, the length 616 is longer than the width 615, and the length 616 is in the stretch direction.

Grips

Figure 13:
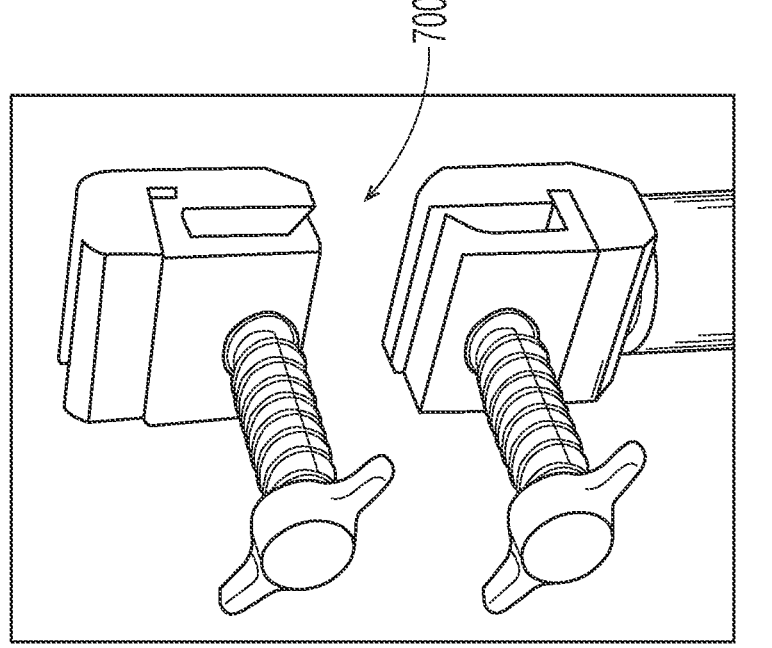

Line contact grips 500 of the type shown in FIG. 12 are used for this test. The line grips 500 are selected to provide a well-defined gauge and avoid undue slippage. The sample is positioned such that it has minimal slack. The apexes 507 of the grips 500 are ground to give good gauge definition while avoiding damage or cutting of the sample. The apexes are ground to provide a radius in the range of 0.5-1.0 mm A portion of one or both grips 500 may be configured to include a material 507 that reduces the tendency of a sample to slip, (e.g., a piece of urethane or neoprene rubber having a Shore A hardness of between 50 and 70). FIG. 13 shows a pair of opposing grips 700 suitable for use herein.

Apparatus

Figure 14:
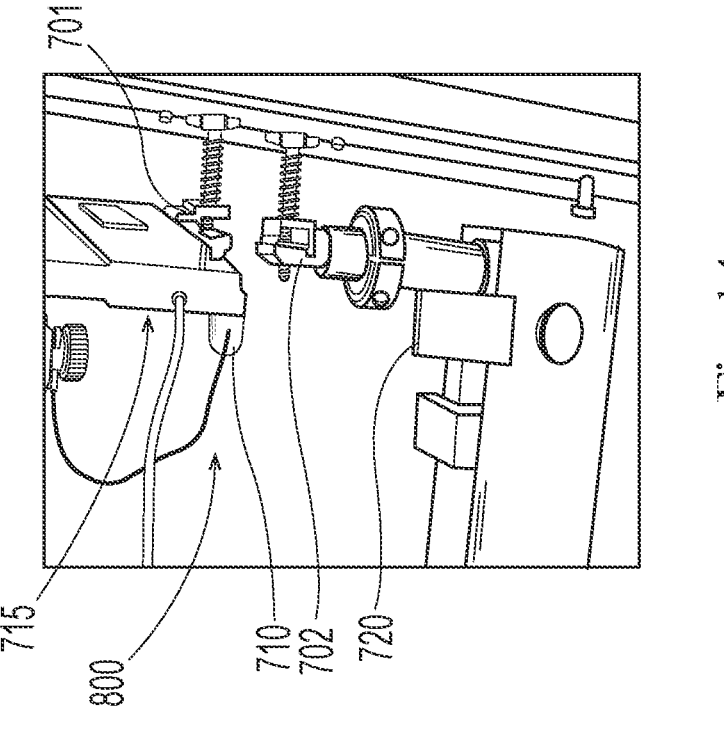
FIGS. 13-14 are schematic perspective views of exemplary equipment for use in the 10-Hour Force Drop/Growth in Aperture Test Method.

The grips are mounted in a frame (e.g., Chatillon MT 150L or similar) that allows hand-operated movement of one grip with respect to the other. Gauge blocks are used to establish precise grip positions for sample loading and sample testing. The entire frame is mounted in a chamber equipped with temperature control equipment well suited for maintaining the air temperature in the immediate proximity of the sample at 37.8° C. FIG. 14 shows an exemplary apparatus 800 for conducting the test. As shown in FIG. 14, the apparatus 800 is set up in a temperature control chamber and includes a top grip 701, a bottom grip 702, a gauge block 720 for precisely positioning at least the bottom grip 702, and a thermocouple 710 for monitoring the temperature in the chamber. A force transducer 715 is deployed in mechanical communication with the top grip 701. The force transducer 715 includes a suitable quality signal conditioner for enabling the desired force measurement without significant drift, noise, etc. The force transducer is selected to provide adequate resolution to identify when the final failure of a sample occurs. The output from the signal conditioner is connected to an analog-to-digital converter interfaced with a computer to allow data acquisition during the test. The force data are sampled at a frequency of at least one data point per second while the sample is being extended and during its initial force decay. The frequency of subsequent data sampling must be sufficient to determine the force decay of a sample over the entire test period (10 hours for "10-Hour Force Drop" and at least 8 hours for "Growth in Aperture"). Time Zero is assigned to the first data point after the sample is extended 100% (i.e., 1 second after extension is complete).

Testing

The grip separation (i.e., gauge length) is set at 25.4 mm and the sample is inserted so that the grips form well-defined lines of contact on the sample. The grip bolts are tightened to provide a secure grip, but without cutting the sample. The temperature chamber door is closed to allow the temperature to equilibrate at target temperature for two minutes. Data acquisition is commenced. The desired displacement (25.4 mm, which is equivalent to 100% strain) is applied to the sample over the course of 15 seconds. Force data that are collected during the test at one-second intervals. Record the force 1 second after straining the sample to 100% as Force at Time Zero. Record the force after 10 hours of holding the sample at 100% strain as the Force after 10 Hrs. The 10-Hour Force Drop means the decay in force from Force at Time Zero to Force after 10 Hours. The 10-Hour Force Drop is calculated as follows:

$$\frac{\text{Force after 10 hrs} - \text{Force at Time Zero}}{\text{Force at time zero}} \times 100$$

For "Growth in Aperture" measurement, the sample is loaded for at least 8 hours and no longer than 10 hours as described above. "Base Aperture Area" is calculated at the beginning of the test. When sample is fully stretched to 100%, dimensions of three apertures that are smallest are measured to 0.1 mm accuracy using caliper. Area of the apertures in the film are measured and not the area of the bond sites. These three apertures will be referred to as base apertures. Once the measurements are completed, chamber doors are closed so the remaining test can be carried out at 37.8 degrees Centigrade. To calculate area of the base apertures, the area is calculated for each of the aperture using the mathematical area formula that best fits the shape of the aperture (rectangle, square, circle, ellipse, etc.). The three calculated areas are then averaged to calculate the "Base Aperture Area". At the end of the test (after 8 hours), the largest aperture dimension is measured using caliper to 0.1 mm accuracy, while sample is still stretched to 100%. "Largest Aperture Area" is the area of the largest aperture in the film of the sample calculated using mathematical area formula that best fits the shape of the aperture. "Growth in Aperture" is calculated using:

$$\frac{\text{Largest Aperture Area} - \text{Base Aperture Area}}{\text{Base Aperture Area}} \times 100$$

Bond Dimension Test Method

The Bond Dimension Test is used to measure various dimensions of bonds in a laminate and Bond Density of a laminate. The Bond Dimension Test is performed on reflected light microscopy images generated using a stereo light microscopy (such as Zeiss V20 Stereoscope) and attached camera (such as the Carl Zeiss AxioCam MRc5). Measurements are performed using Image Pro Plus software (Version 7.0.0.591, Media Cybernetics, USA) calibrated against a ruler that was placed within the image when it was acquired. For purposes of this method, a bond is the intentional joining of two or more layers and is the deformed area caused during the bonding process (e.g., the reduced caliper at the site of bonding).

Identify a plurality of bonds of interest from the uniform bond pattern area and outline the resulting periphery in a rectilinear specimen of at least 1 $cm^2$ area and collect by cutting along the periphery. Care should be taken to avoid collecting specimen from an adjacent region if it is different (e.g., unbonded, inelastic or area with different bond pattern). The specimen is collected in a substantially rectangular shape having at least a 1 $cm^2$ area. If a sufficiently large sample is not available, a smaller sample with a minimum of one repeat unit of repeating bond pattern can be used, and the measured bond area values are normalized to the 1 $cm^2$ specimen area. If the pattern is too large for stereoscope imaging, a SLR Camera (such as Pentax R20D) or scanner (such as Epson Perfection V750 Pro Flatbed Scanner) with a black background behind sample should be used to collect the image.

Fully stretch the specimen. For corrugated laminates, the specimen is fully stretched when corrugations are substantially flattened by extending the laminate while making sure that the inelastic substrates of the laminate are not plastically deformed. For laminates without corrugations, the specimen is considered fully stretched without such extension.

A ruler is placed in each image parallel to the bonds longitudinal direction when the image was acquired. Dimensions of a discrete bond and the Discrete Bond Area are measured with the irregular area tool in Image Pro Plus software by selecting only the bonded regions.

Aspect Ratio of Discrete $$\text{Bond} = \frac{\substack{\text{Greatest dimension of complete}\\ \text{discrete bond in specimen, mm}}}{\substack{\text{Dimension normal to the greatest dimension}\\ \text{of the same complete discrete bond, mm}}}$$

All Discrete Bond Areas within the specimen are added to calculate Aggregate Bond Area for the specimen and then the Aggregate Bond Area is divided by the area of the specimen (as measured in the fully stretched condition) to determine bond density, and can be expressed with the following formula:

$$\text{Bond Density } \% = \left( \frac{\text{Aggregate Bond Area, mm}^2}{\text{Specimen Area, mm}^2} \right) \times 100\%$$

Hysteresis Test Method

The Hysteresis Test can be used to various specified strain or load values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut to dimensions listed in the table below for the test performed.

Test Protocol

1. Select the appropriate line grips (similar to those disclosed above under Grips Section of the 10-Hour Force Drop/Growth in Aperture Test Method) and load cell. The grips must have one flat surface and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used. Calibrate the tester according to the manufacturer's instructions.

2. Set the distance between the grips (gauge length) as per the test performed (table below).

3. Place the specimen in the flat surfaces of the grips such that the uniform width lies along a direction perpendicular to the gauge length direction. Secure the specimen in the upper grip, let the specimen hang slack, then close the lower grip.

4. Pre-load: Set the slack pre-load at 0.05N, and pre-load crosshead speed of 13 mm/min. This means that the data collection starts when the slack is removed (at a constant crosshead speed of 13 mm/min) with a force of 0.05N. Strain is calculated based on the adjusted gauge length ($l_{ini}$), which is the length of the specimen in between the grips of the tensile tester at a force of 0.05N. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the given load or strain at a constant cross head speed as defined in the table below for the test. Report the stretched specimen length between the grips as $l_{max}$.

5(b) First cycle unloading: Hold the specimen at the load or strain of step 5(a) for 30 seconds and then return the crosshead to its starting position (0% strain or initial sample length, $l_{ini}$) at a constant cross head speed defined in step 5(a) above.

5(c) Hold the specimen in the unstrained state for 1 minute.

5(d) Second cycle: Repeat Step 5(a) and 5(b).

| | Elastic and Extensible Tests | Laminate Performance Test |
|---|---|---|
| Sample Length in the stretch direction (mm) | ≥7 | ≥26 |
| Sample Width, perpendicular to stretch direction (mm) | 25.4 preferred (10 mm minimum) | 25.4 |
| Gauge Length (mm) | 7 | 25.4 |
| Test Speed (in/min) | 10 | 10 |
| Load for Step 5(a) | N/A | 4N |
| Strain % for Step 5(a) | 50% | N/A |

A computer data system records the force exerted on the sample during the test as a function of applied strain. From the resulting data generated, the following quantities are reported.

i. Length of specimen between the grips at a slack preload of 0.05N ($l_{ini}$) to the nearest 0.001 mm.

ii. Length of specimen between the grips on first cycle at the at a given strain ($l_{max}$) to the nearest 0.001 mm.

iii. Length of specimen between the grips at a second cycle load force of 0.07N ($l_{ext}$) to the nearest 0.001 mm.

iv. Force at 50% strain during the first load cycle to the nearest 0.01 N/in (reported as Load Force at 50%)

v. Force at 50% strain during the second unload cycle to the nearest 0.01 N/in (reported as Unload Force at 50%)

Load Force and Unload Force values reported are converted into MPa using the following formula, provided basis weight of the elastomeric layer is known or calculated from other known information:

$$\text{Load or Unload (MPa)} = \left( \frac{\text{Load or Unload } \left(\frac{N}{in}\right) * \text{Density} \left(\frac{g}{cm3}\right) * 1000}{25.4 * \text{Elastomeric Layer } BW(gsm)} \right)$$

If the density of the elastomeric layer is unknown then 0.93 g/cm³ density value is used.

If the average elastomeric layer's thickness can be evaluated via any laboratory methods (such as SEM) then Load Force and Unload Force values reported can be converted into MPa using the following formula:

Load or Unload (MPa) =

$$\left( \frac{\text{Load or Unload } \left(\frac{N}{in}\right)}{25.4 * \text{measured average Elastomeric layer thickness (mm)}} \right)$$

Air Permeability Test Method

The air permeability of an ear laminate or substrate (e.g., film, nonwoven, or article component) is determined by measuring the flow rate of standard conditioned air through a test specimen driven by a specified pressure drop. This test is particularly suited to materials having relatively high permeability to gases, such as nonwovens, apertured ear laminates and the like. ASTM D737 is used, modified as follows.

A TexTest FX 3300 instrument or equivalent is used, available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The specimen is tested while in a relaxed state.

The test pressure drop is set to 500 Pascal and the 1 cm² area test head (model FX 3300-5) or equivalent is used. The result is recorded to three significant digits. The average of 5 specimens is calculated and reported as the Breathability Value (m³/m²/min).

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 10). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a front waist region, a rear waist region and a crotch region disposed between the front waist region and the rear waist region;
    a topsheet, a backsheet and an absorbent core disposed between the topsheet and the backsheet; and a stretch laminate comprising a bonding region comprising a plurality of ultrasonic bonds, wherein each of the plurality of ultrasonic bonds comprises a major dimension and a minor dimension, wherein a majority of the ultrasonic bonds are oriented in a stretch direction such that the major dimension is parallel to a stretch direction, and wherein each ultrasonic bond in the plurality comprises at least one dimension that is 0.7 mm or greater;
    wherein the bonding region comprises a Hysteresis Ratio of 2.5 or less and an Unload Force at 50% of 0.44 MPa or greater.

2. The absorbent article of claim 1 wherein the bonding region comprises a Hysteresis Ratio of 2.4 or less.

3. The absorbent article of claim 1 wherein the stretch laminate comprises a Bond Density of at least 1.5%.

4. The absorbent article of claim 1 wherein a majority of the stretch direction oriented bonds comprise an aspect ratio of at least 1.25.

5. The absorbent article of claim 1 wherein the stretch laminate comprises one or more reinforcing features, wherein the reinforcing features are selected from the group consisting of additional bonds, layers, folds, substrates and combinations thereof.

6. The absorbent article of claim 1 wherein the stretch laminate is disposed in a component selected from the group consisting of an ear, a waistband, a belt and combinations thereof.

7. An absorbent article comprising:
    a first waist region, a second waist region and a crotch region disposed between the first and second waist regions;
    a topsheet, a backsheet and an absorbent core disposed between the topsheet and the backsheet; and
    a stretch laminate, wherein the stretch laminate comprises:
        a first bonding region having a first plurality of ultrasonic bonds, wherein each bond in the first plurality comprises a major dimension and a minor dimension and are oriented such that the major dimension is substantially parallel to a stretch direction; and
        a second bonding region having a second plurality of bonds, wherein the majority of bonds in the second plurality are oriented in a second direction, the second direction being substantially perpendicular to the stretch direction,
        wherein the second bonding region comprises a Low Stress Region, and
        wherein a total bond area of the first plurality of ultrasonic bonds is greater than a total bond area of the second plurality of bonds.

8. The absorbent article of claim 7 wherein the Low Stress Region comprises a Load Force at 50% of about 1.46 MPa or less.

9. The absorbent article of claim 7 wherein the second plurality is at least partially interspersed or overlapping relationship with the first plurality.

10. The absorbent article of claim 7 wherein the stretch laminate comprises a Bond Density of at least 1.5%.

11. The absorbent article of claim 7 wherein at least some of the stretch direction oriented bonds comprise an aspect ratio of at least 1.25.

12. The absorbent article of claim 7 wherein the stretch laminate comprises one or more reinforcing features, wherein the reinforcing features are selected from the group consisting of additional bonds, layers, folds, substrates and combinations thereof.

13. The absorbent article of claim 7 wherein the second plurality of bonds comprises a plurality of ultrasonic bonds.

14. An absorbent article comprising:
a first waist region, a second waist region and a crotch region disposed between the first and second waist regions;
a topsheet, a backsheet and an absorbent core disposed between the topsheet and the backsheet; and
a stretch laminate, the stretch laminate comprising:
a nonwoven layer and a film;
a bonding region having a plurality of ultrasonic bonds, wherein each of the plurality of ultrasonic bonds comprises a major dimension and a minor dimension, wherein a majority of the plurality of ultrasonic bonds are oriented in a stretch direction such that the major dimension is parallel to a stretch direction, and wherein each of the plurality of ultrasonic bonds comprise an aspect ratio of at least about 1.25;
a 10-Hour Force Drop of 65% or less, and
a Growth in Aperture of 50% or less.

15. The absorbent article of claim 14 wherein each of the ultrasonic bonds oriented in the stretch direction comprise an elliptical shape.

16. The absorbent article of claim 14 wherein the laminate comprises a Hysteresis Ratio of 2.4 or less.

17. The absorbent article of claim 14 wherein the bonding region further comprises one or more bonds oriented in a second direction, the second direction being perpendicular to the stretch direction.

18. The absorbent article of claim 17 wherein each of the bonds oriented in the second direction comprises a major dimension length of 1.2 mm or less.

19. The absorbent article of claim 17 wherein the bonding region comprises at least 25% of bonds oriented in the second direction.

20. The absorbent article of claim 14 wherein the stretch laminate comprises one or more reinforcing features, wherein the reinforcing features are selected from the group consisting of additional bonds, layers, folds, substrates and combinations thereof.

* * * * *